(12) United States Patent
Bosworth et al.

(10) Patent No.: US 10,736,755 B2
(45) Date of Patent: Aug. 11, 2020

(54) MENISCAL TRANSPLANT SYSTEM

(71) Applicant: Conmed Corporation, Utica, NY (US)

(72) Inventors: Adrian E. Bosworth, Bradenton, FL (US); Peter C. Miller, Largo, FL (US)

(73) Assignee: Conmed Corporation, Utica, NY (US)

( * ) Notice: Subject to any disclaimer, the term of this patent is extended or adjusted under 35 U.S.C. 154(b) by 195 days.

(21) Appl. No.: 16/040,708

(22) Filed: Jul. 20, 2018

(65) Prior Publication Data
US 2018/0325699 A1 Nov. 15, 2018

Related U.S. Application Data

(62) Division of application No. 15/074,982, filed on Mar. 18, 2016, now Pat. No. 10,034,778.

(60) Provisional application No. 62/135,772, filed on Mar. 20, 2015.

(51) Int. Cl.
| | |
|---|---|
| *A61B 17/17* | (2006.01) |
| *A61F 2/46* | (2006.01) |
| *A61F 2/38* | (2006.01) |
| *A61B 17/04* | (2006.01) |
| *A61F 2/28* | (2006.01) |
| *A61B 17/16* | (2006.01) |
| *A61B 17/00* | (2006.01) |
| *A61B 90/00* | (2016.01) |

(52) U.S. Cl.
CPC ............ *A61F 2/4644* (2013.01); *A61B 17/04* (2013.01); *A61B 17/1675* (2013.01); *A61B 17/1764* (2013.01); *A61F 2/28* (2013.01); *A61F 2/3872* (2013.01); *A61B 17/1604* (2013.01); *A61B 2017/00969* (2013.01); *A61B 2090/036* (2016.02); *A61B 2090/062* (2016.02); *A61F 2002/4645* (2013.01); *A61F 2002/4658* (2013.01)

(58) Field of Classification Search
CPC ....... A61B 17/1764; A61B 2017/00969; A61F 2/3872; A61F 2/4644
See application file for complete search history.

(56) References Cited

U.S. PATENT DOCUMENTS

| | | | | |
|---|---|---|---|---|
| 2004/0220578 | A1* | 11/2004 | Bagga | A61B 17/15 606/87 |
| 2013/0096680 | A1* | 4/2013 | Ribeiro | A61F 2/3872 623/14.12 |

* cited by examiner

*Primary Examiner* — Samuel S Hanna
(74) *Attorney, Agent, or Firm* — Bond, Schoeneck & King, PLLC

(57) ABSTRACT

A workstation having a pair of posts on either side of a clamping plate where a donor bone may be placed on sequentially cut in three separate cutting paths. Cutting gates are attached to the posts and used to provide cutting paths that can be precisely oriented with respect to the meniscus of the donor bone part using visual alignment without any manual measurements. The graft is affixed to a machining clamp and shaved to appropriately shape the sides and form a radius on the bottom of the graft. A tibia is then prepared by using a drill guide to form a pilot hole and then to drill out a large hole for the graft. The drilled hole is expanded and shaped using a rod guide and chisel and then a rasp. The shaped graft may then be implanted into the shaped hole and sutured in place.

7 Claims, 33 Drawing Sheets

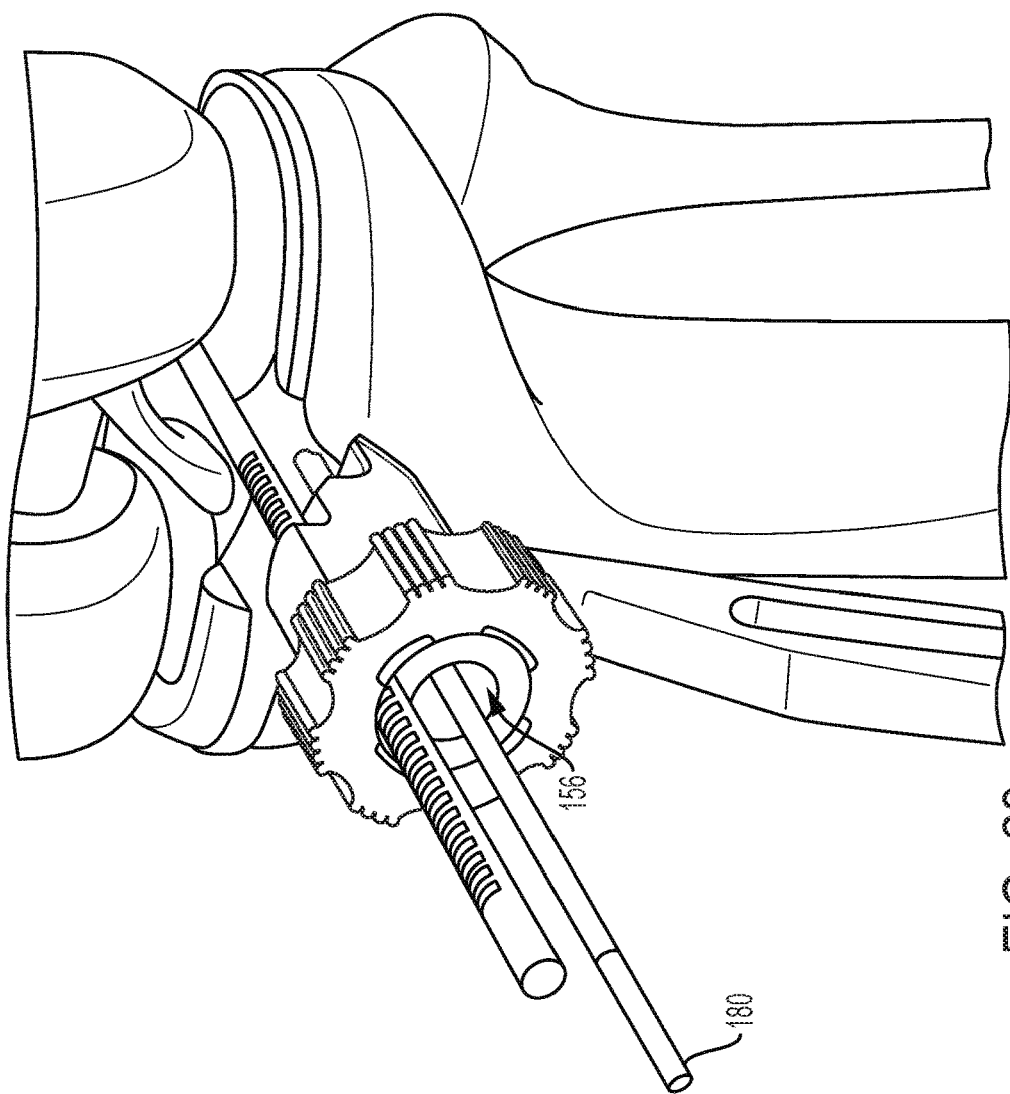
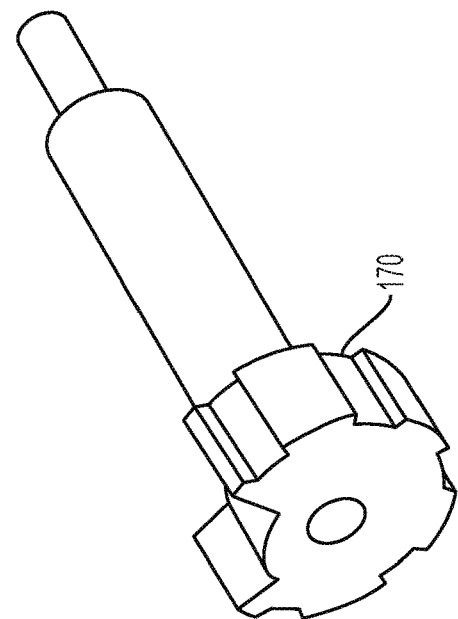
FIG. 23

MENISCAL TRANSPLANT SYSTEM

CROSS-REFERENCE TO RELATED APPLICATIONS

This application is a divisional and claims priority to U.S. Non-Provisional application Ser. No. 15/074,982, filed on Mar. 18, 2016 which claims priority to U.S. Provisional Application No. 62/135,772, filed on Mar. 20, 2015, each of which is hereby incorporated by reference in its respective entirety.

BACKGROUND OF THE INVENTION

1. Field of the Invention

The present invention relates to meniscal transplant systems, and, more particularly, to a meniscal transplant workstation and accompanying tools for preparing a meniscal transplant and tibial surface and mounting the transplant to a tibia.

2. Description of the Related Art

A damaged human knee joint meniscus may be repaired using a meniscus implant and integral bone bridge that is shaped to be inserted into a corresponding groove cut in the tibia. As the size, shape and cuts of donor implants vary widely, the implant may be positioned in a workstation so that it can be appropriately shaped using surgical saws and rasps. Conventional workstations, however, require that the user manually determine the appropriate measurements and cuts to be performed on the implant and the knee joint to be repaired. As the site preparation for the implant is also performed manually, it is often difficult to achieve an exact match between the prepared implant and the prepared site. Accordingly, there is a need in the art for a graft workstation and associated instruments that improve the ease and accuracy by which such implants and repairs can be made.

BRIEF SUMMARY OF THE INVENTION

The present invention is a system for preparing and implanting a meniscus allograft and integral bone bridge. The invention includes a workstation having a base and a pair of posts extending upwardly from the base to define an axis therebetween. A plate is positioned between the posts to define a horizontal plane. A clamp having an arm extending over the plate may be used to hold a donor bone in place. A first cutting gate may be removably coupled to the pair of posts to define a first cutting path that extends along a first plane that intersects with the horizontal plane of the plate and that is proximally offset from the axis of the pair of posts. A second cutting gate may be removably coupled to the pair of posts to define a second cutting path that extends along a second plane that is perpendicular to vertical, wherein the second cutting gate may be adjusted to orient the second plane into or out of parallel with the horizontal plane. A third cutting gate may be removably coupled to the pair of posts to define a third cutting path that extends along a third plane that intersects with the horizontal plane of the plate and that is distally offset from the axis of the pair of posts. In one embodiment, the third cutting gate comprises the first cutting gate reversibly coupled to the posts. A depth setting groove may extend along the base of the workstation. The invention also includes a clamp configured to be attached to a graft positioned in the depth setting groove. The clamp is used to machine the graft using a first shaver having a first set of blades for shaping the graft into a first shape. The clamp is also used to machine the graft using a second shaver having a second set blades for shaping the graft into a second shape that is different than the first shape. The workstation may further include a measuring groove having a profile that corresponds to the first and second shapes extending along the base and having indicia positioned therealong for measuring the length of a graft positioned in the measuring groove.

For installing the graft in a tibia, the invention comprises a drill guide having a throughbore and an adjustable hook beam that extends from a proximal end through the drill guide proximately to the throughbore to a distal end that may be affixed over a tibia into which a graft is to be implanted. A pilot guide may be inserted into the throughbore of the drill guide and a pilot drill bit having a pilot drill stop can be extended through the pilot guide until the pilot drill stop contacts the proximate end of the hook beam. A guide pin can be extended through the throughbore of the drill guide and a cannulated drill bit having drill stop can be extended through the pilot guide and over the guide pin until the drill stop contacts the proximate end of hook beam to form an implant hole in the tibia into which the graft is to be implanted. A guide rod may be positioned in the implant hole and a chisel having a handle that can slidingly advance along the guide rod into the tibia to shape the implant hole until the guide rod extends into the handle of the chisel a predetermined distance. A rasp having a cross-section corresponding to the cross-sectional shape of the graft that may be advanced into the shaped implant hole to shape the hole to exactly match the graft prepared using the workstation of the present invention.

The invention comprises a method for preparing a meniscus bone graft. A donor bone part having a meniscus extending from a pair of meniscal horns is clamped between a plate extending along a horizontal plane and a clamp of a workstation. A first cutting gate is positioned over a pair of posts extending upwardly from the workstation on either side of the plate to define an axis therebetween. The donor bone part is cut along a first cutting path defined by the first cutting gate that extends along a first plane that intersects with the horizontal plane of the plate and that is proximally offset from the axis of the pair of posts. A second cutting gate is positioned over the pair of posts and aligning along the axis that extends between the pair of meniscal horns. The donor bone part is then cut along a second cutting path defined by the second cutting gate. A third cutting gate is positioned over the pair of posts and the donor bone part is cut in a third cutting path defined by the third cutting gate that extends along a third plane which intersects with the horizontal plane of the plate and that is distally offset from the axis of the pair of posts. A graft is thereby formed having three sides defined by the three cutting paths, a native top side having the meniscus naturally attached to the bone implant by its meniscal horns. The graft is then placed into a groove and a clamp is attached to set a predetermined protrusion for the graft. The clamp containing the graft is placed in a slot in the first shaver and moved along a first set of blades to shape the graft into a first shape. The clamp is also used to move the graft along a second shaver having a second set of blades to shape the graft into a second shape that is different than the first shape. The size of the graft can then be checked by placing it in a second groove of the workstation.

The graft may then be implanted by attaching a transtibial drill guide having a throughbore and an adjustable hook beam that extends through the drill guide from a proximal end to a distal end positioned over a tibia into which the graft is to be implanted. A pilot guide is inserted into the throughbore of the drill guide and a pilot drill bit having a pilot drill stop is used to drill a pilot hole into the tibia until the pilot drill stop contacts the proximate end of the hook beam. A guide pin is extended through the throughbore of the drill guide and the pilot hole and a cannulated drill bit having drill stop that can be extended through the pilot guide and over the guide pin is used to form an implant hole in the tibia. A guide rod is positioned in the implant hole and a chisel having a handle that can slidingly advance along the guide rod into the tibia is used to shape the implant hole until the guide rod extends into the handle of the chisel a predetermined distance. A rasp having a cross-section corresponding to the cross-sectional shape of the graft is then used to shape the implant hole. The graft is then inserted into the implant hole and the meniscus sutured to the tibia.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 23 is a perspective view of drill guide with pilot drill guide partially removed according to the present invention;

DETAILED DESCRIPTION OF THE INVENTION

Figure 1:
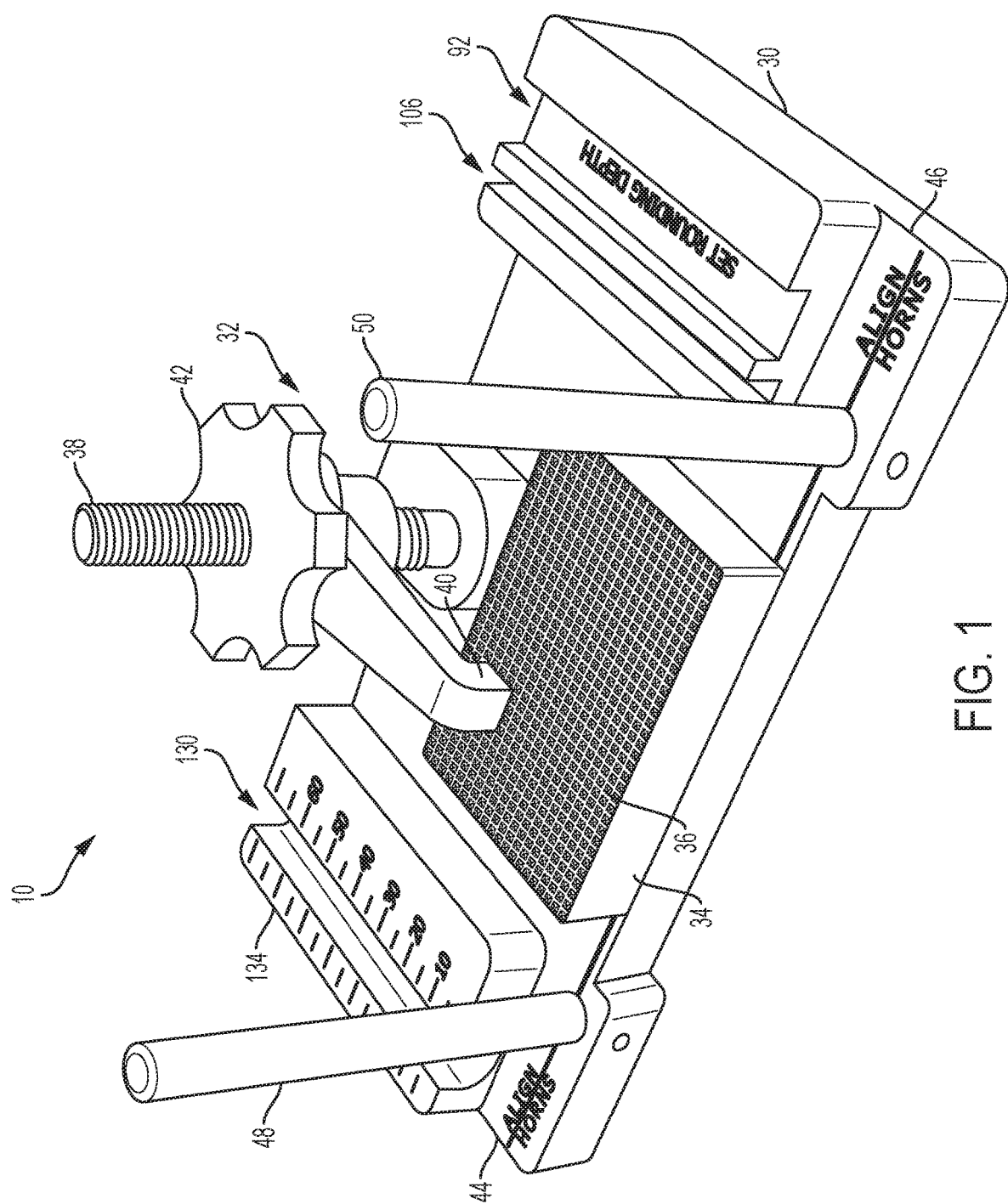
FIG. 1 is a perspective view of a workstation according to the present invention.
Figure 2:
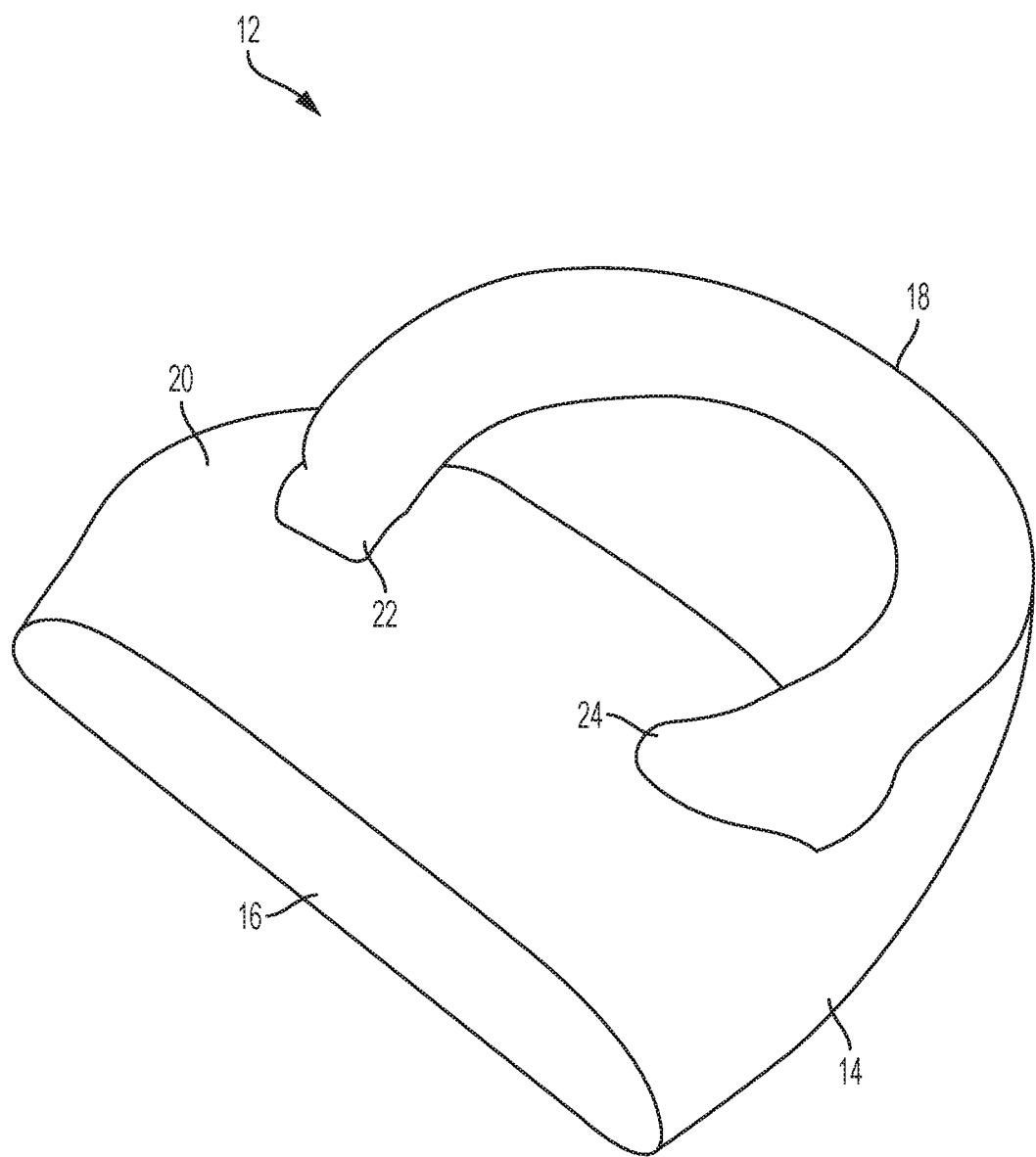
FIG. 2 is a perspective view of a donor bone graft to be prepared on a workstation according to the present invention.

Referring to the drawings, wherein like numerals refer to like parts throughout, there is seen in FIGS. 1 and 2 a workstation 10 for preparing an allograft donor bone graft 12 for implantation into the tibia of a patient. Graft 12 typically comprises a hemi-tibial plateau bone portion 14 having a saw cut surface 16 and an attached meniscus 18 extending from the top side 20 of bone portion 14 via two meniscal attachment horns 22 and 24.

Figure 3:
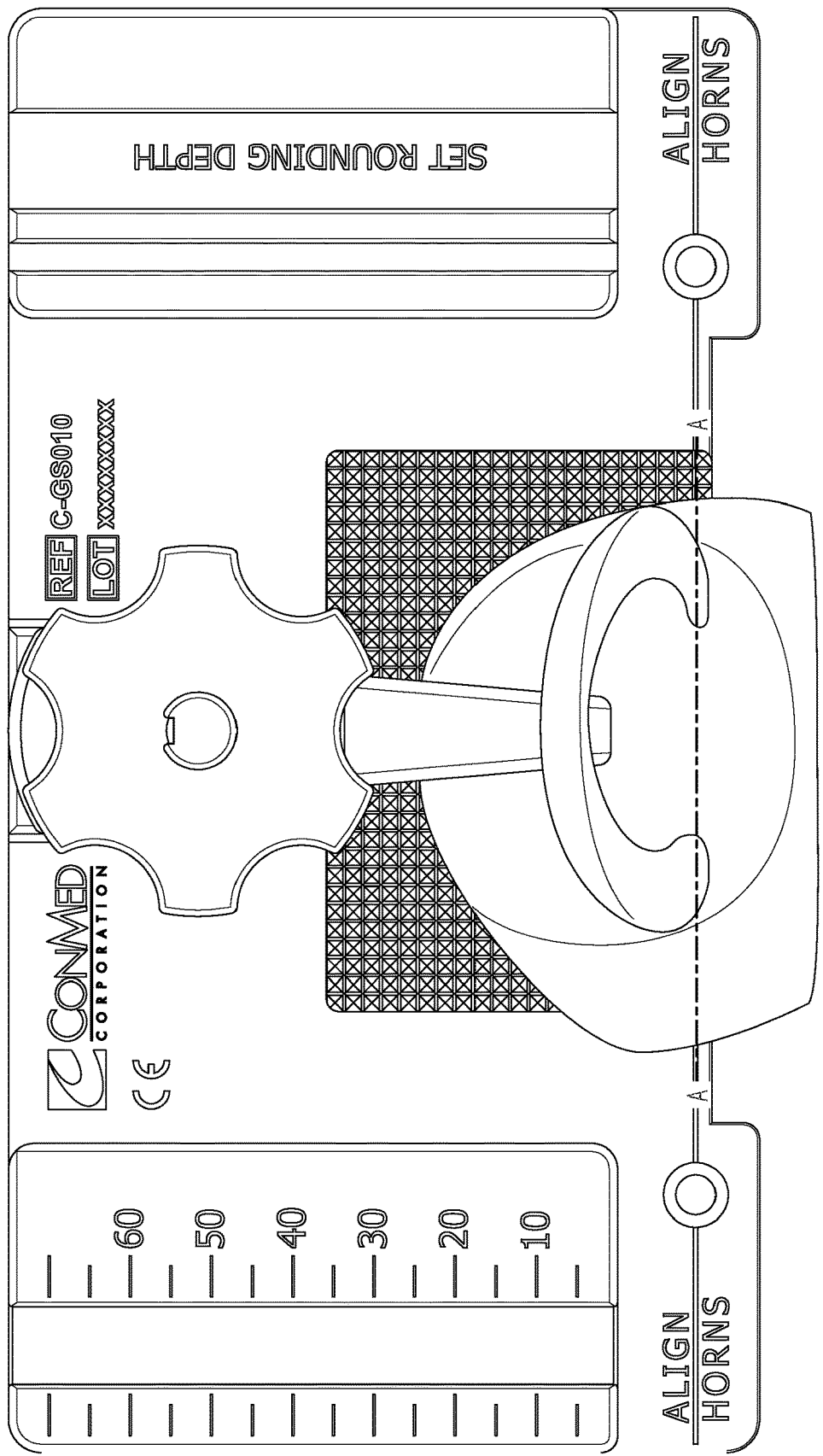
FIG. 3 is a perspective view of a donor bone graft positioned on a workstation according to the present invention.

Workstation 10 comprises a base 30 supporting a clamp 32 aligned over a central plate 34 having surface 36 with features, such as checkering or texturing that is machined therein, so that graft 12 can be securely clamped in place on workstation 10. Clamp 32 comprises a threaded post 38 extending upwardly from base 30, a clamping arm 40 coupled to post and extending over plate 34, and a threaded wheel 42 that can be advanced up or down post 38 via rotational movement to bring clamping arm 40 into secure engagement with graft 12 when it is positioned on plate 34. Post 38 may be keyed to arm 40 so that arm 40 does not rotate around post 38. Referring to FIG. 3, base 30 further includes visual alignment indicia 44 and 46 for use in aligning the two meniscal horns 22 and 24 (shown as disposed along axis A-A on graft 12) therewith when graft 12 is placed onto plate 34 and clamped in place by clamp 32. Base 30 additionally supports a pair of guide posts 48 and 50 that are positioned on opposing sides of and proximately of plate 36. When graft 12 is properly positioned on plate 34 and clamped in place by clamp 32, saw cut 16 of graft 12 will extend over the proximate edge of plate 36 between guide posts 48 and 50. In this manner, workstation 10 allows graft 12 to be easily aligned for subsequent cutting operations to form an implant with precise dimensions for insertion into a similarly dimensioned receiving trough formed into the tibia of a patient.

Figure 4:
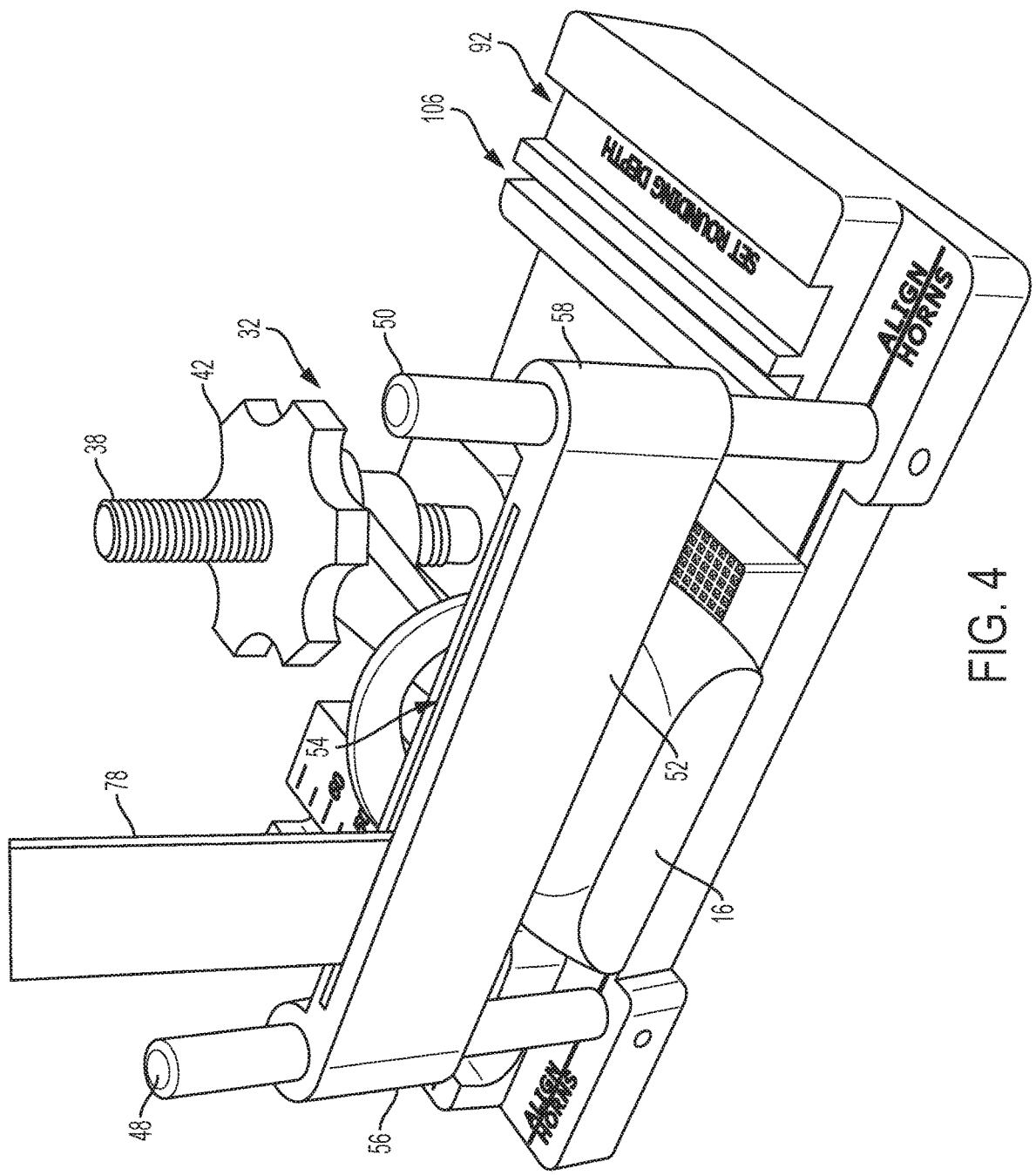
FIG. 4 is a perspective view of a first cutting fence on a workstation according to the present invention.

Referring to FIG. 4, a first cutting gate 52 having a slot 54 formed therein for accepting an oscillating planar saw blade 78 may be positioned over graft 12 by mounting it on posts 48 and 50 of base 30. First cutting gate 52 includes a pair of bosses 56 and 58 positioned at either end thereof that are adapted to accept guide posts 48 and 50, respectively, so that cutting gate 52 is securely held above graft 12. Bosses 56 and 58 may be keyed to posts guide posts 48 and 50 to prevent improper installation of first cutting gate 52. First cutting gate 52 is used to guide saw blade 78 to form a first cutting path along the front of graft 12 that is parallel to the axis A-A of meniscal horns 22 and 24. Saw cut 16, which can be very irregular and imprecise when it is formed to remove graft 12 from the tibia of a donor, is removed and replaced with a new cut that is precisely oriented relative to meniscal horns 22 and 24. Slot 54 of first cutting gate 52 is also oriented so that the first cutting path is angled slightly away from vertical so the newly formed cut in graft 12 has a slight bevel and is wider toward the bottom side of graft 12 relative to meniscal horns 22 and 24 on the top side 20 of graft 12. Preferably, first cutting gate 52 provides a first cutting path that is offset from vertical by about five degrees. Slot 54 of first cutting gate 52 is also offset from the axis of posts 48 and 50 so that the resulting cut proximate to the axis of posts 48 and 50 a predetermined distance, as well as parallel thereto. As a result, the result cut along first cutting path will be a predetermined distance in front of meniscal horns 22 and 24, which are intended to be aligned so that their axis A-A is aligned along the axis of posts 48 and 50 and the indicia provided therewith. The amount of offset is preferably one-half of the desired width of the final prepared graft 12 because, as explained below, first cutting gate 52 may also be used to form the opposite face of graft 12. In the example illustrated in the present application, the offset is five millimeters to produce a final graft 12 having a width of ten millimeters.

Figure 5:
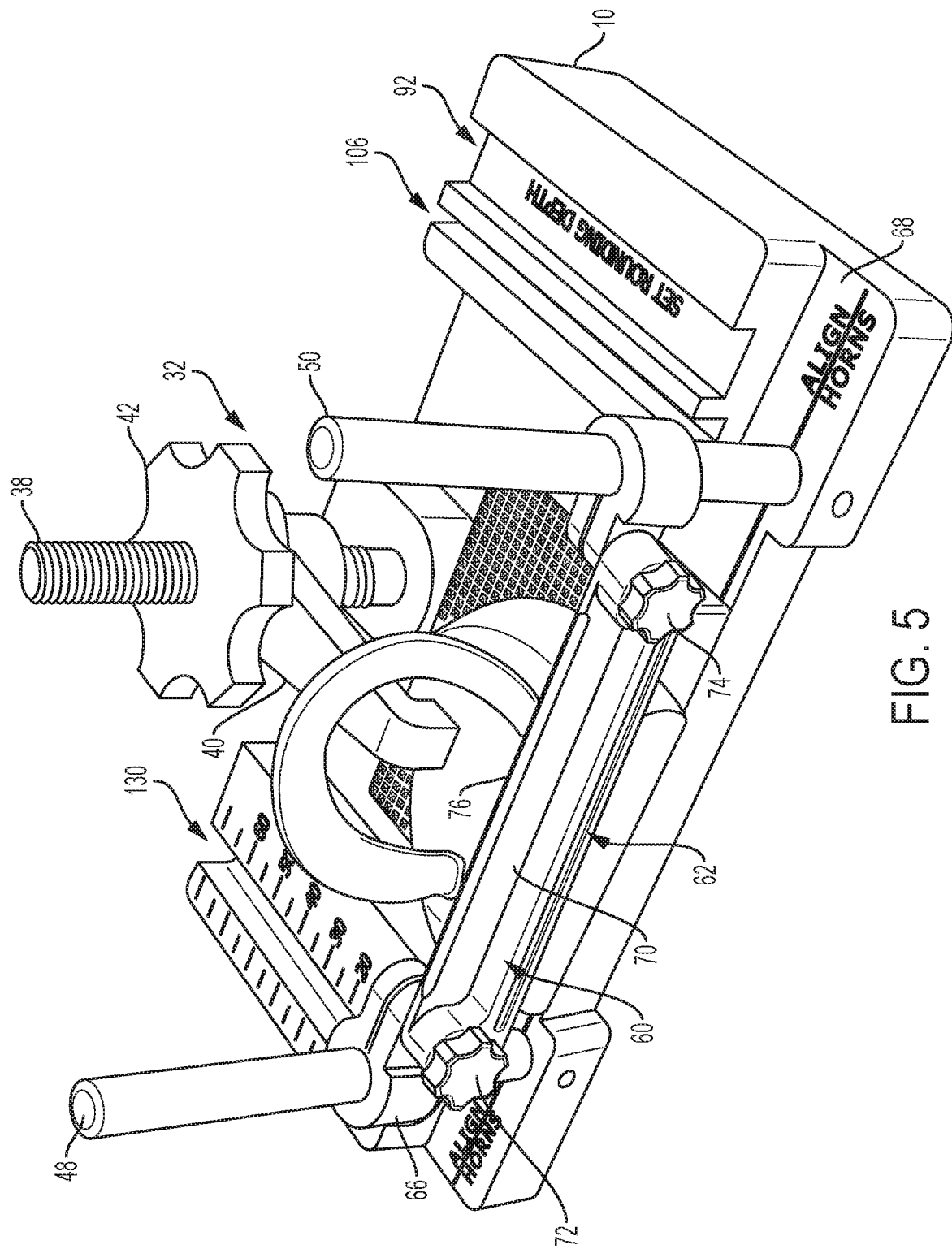
FIG. 5 is a perspective view of a second cutting fence on a workstation according to the present invention.
Figure 6:
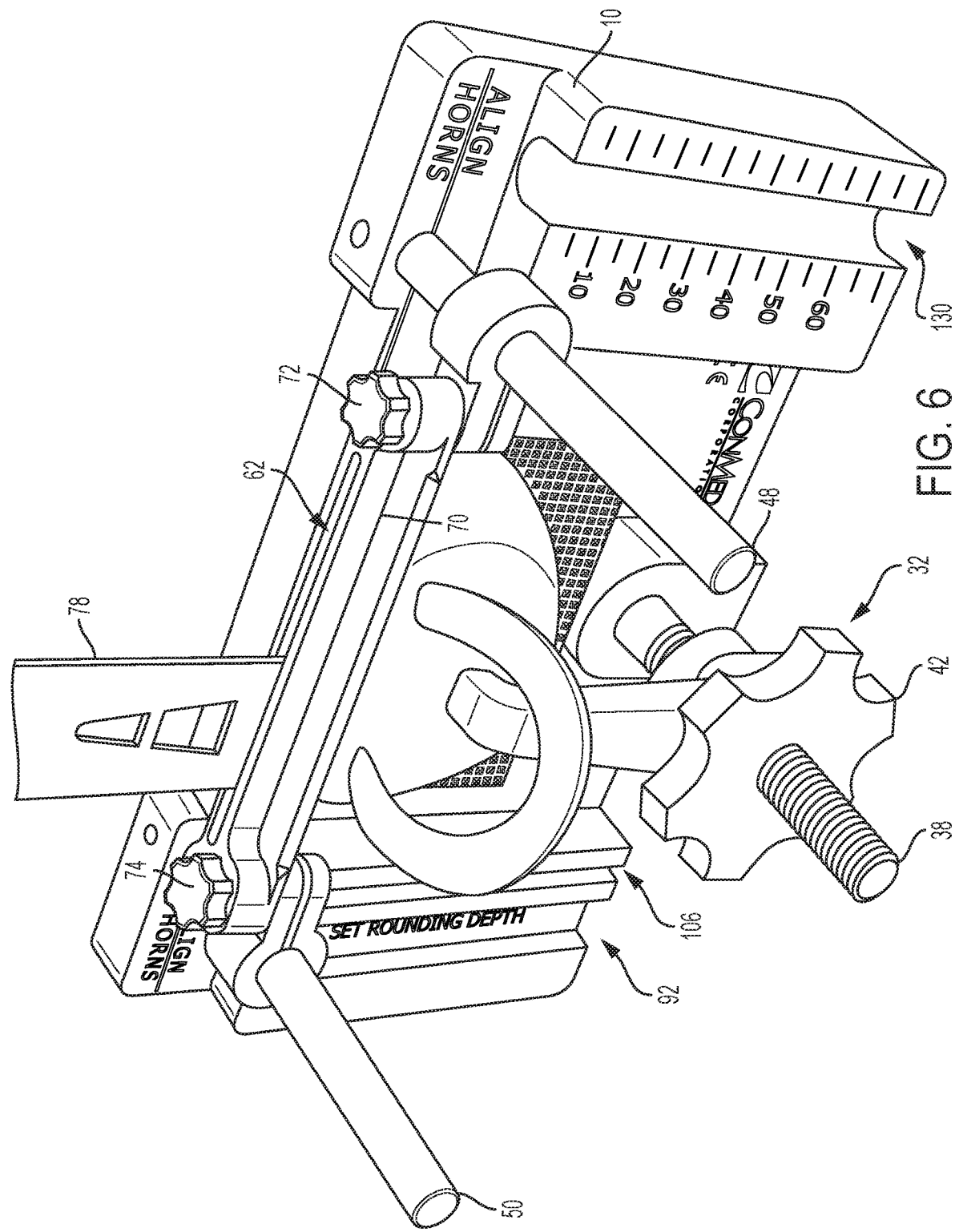
FIG. 6 is another perspective view of a second cutting fence on a workstation according to the present invention.

Referring to FIG. 5, a second cutting gate 60 having a slot 62 formed therein for accepting a saw blade 78 may be positioned over graft 12 using a pair of bosses 66 and 68 at either end that are adapted to accept guide posts 48 and 50, respectively. Slot 62 of second cutting gate 60 is formed in a movable fence 70 interconnected to bosses 66 and 68 by a pair of knobs 72 and 74 that may be rotated to loosen and tighten the connection between fence 70 and bosses 66 and 68 so that fence 70 can be pivoted relative to bosses 66 and 68 so that the upper edge 76 of fence 70 can be aligned with meniscal horns 22 and 24. Fence 70 may thus be oriented along an axis that is non-perpendicular the axis of posts 48 and 50 using the upper edge 76 of fence 70 as a visual guide to define a cutting path that extends along a plane that is parallel to the axis formed by meniscal horns 22 and 24, which may not be parallel to surface 36 of plate 36. The height of fence 70 may thus be dimensioned so that, once upper edge 76 is aligned with meniscal horns 22 and 24, slot 62 will be positioned a predetermined distance downwardly from meniscal horns 22 and 24. For example, upper edge 76 of fence 70 can be used to align a cutting path that is precisely 11 millimeters below upper surface 20 of graft 12, which avoid the need for hand measuring and pen marking common in the field for this particular cut. Slot 62 of second cutting gate 60 thus produces a second cut in graft 12 that accurately and precisely defines a predetermined depth for graft 12 that is also parallel to the axis formed by meniscal horns 22 and 24 due to the alignment of fence 70 with meniscal horns 22 and 24. As seen in FIG. 6, workstation 10 may be reoriented so that saw blade 78 can be inserted downwardly into slot of second cutting gate 60 and used to cut graft 12. Saw blade 78 can be inserted past the distance necessary to define the depth of graft 12 as a subsequent cut will detach the desired graft 12 and associated meniscus 18 from the surrounding bone of original graft 12.

Figure 7:
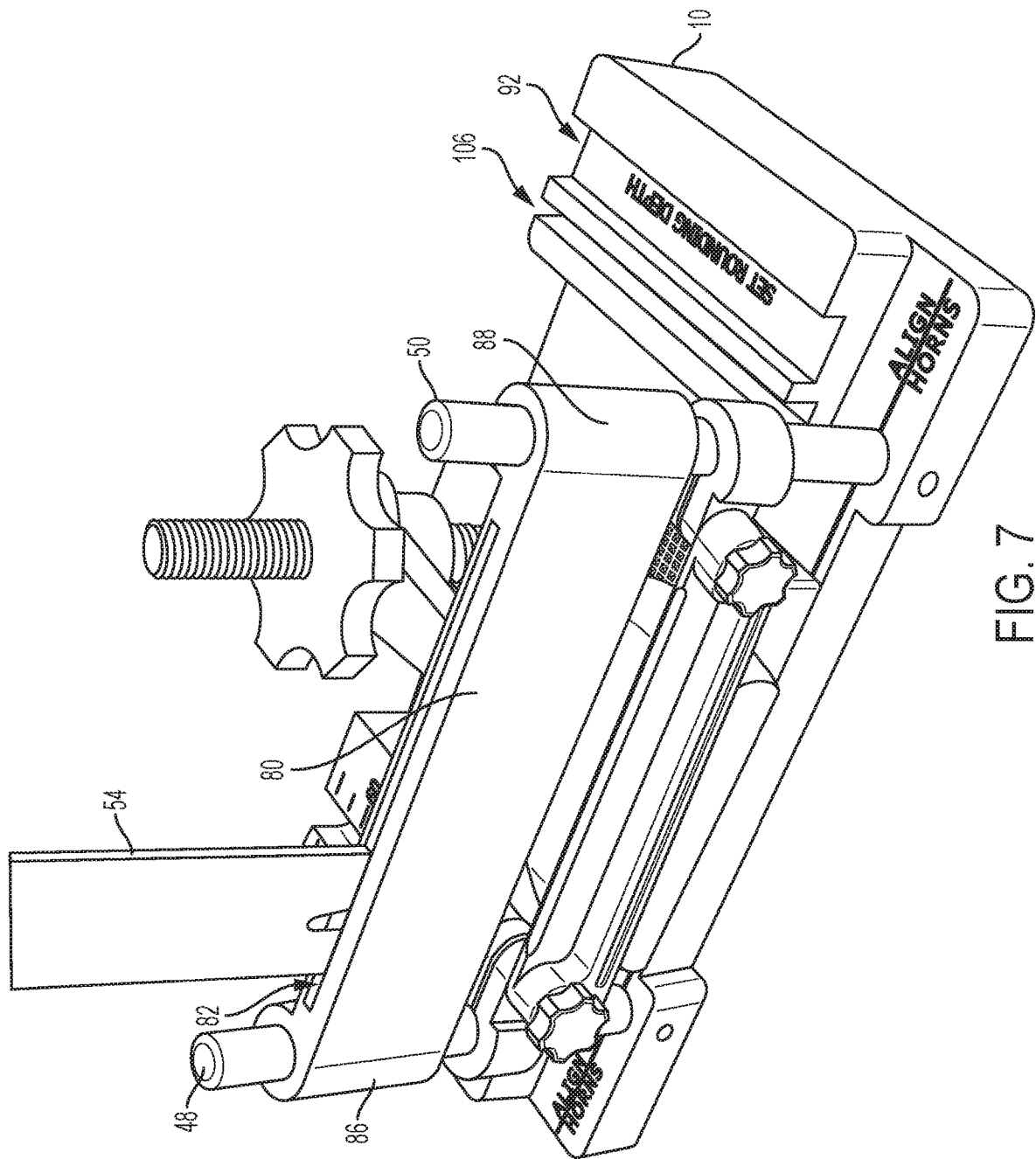
FIG. 7 is a perspective view of a third cutting fence on a workstation according to the present invention.
Figure 8:
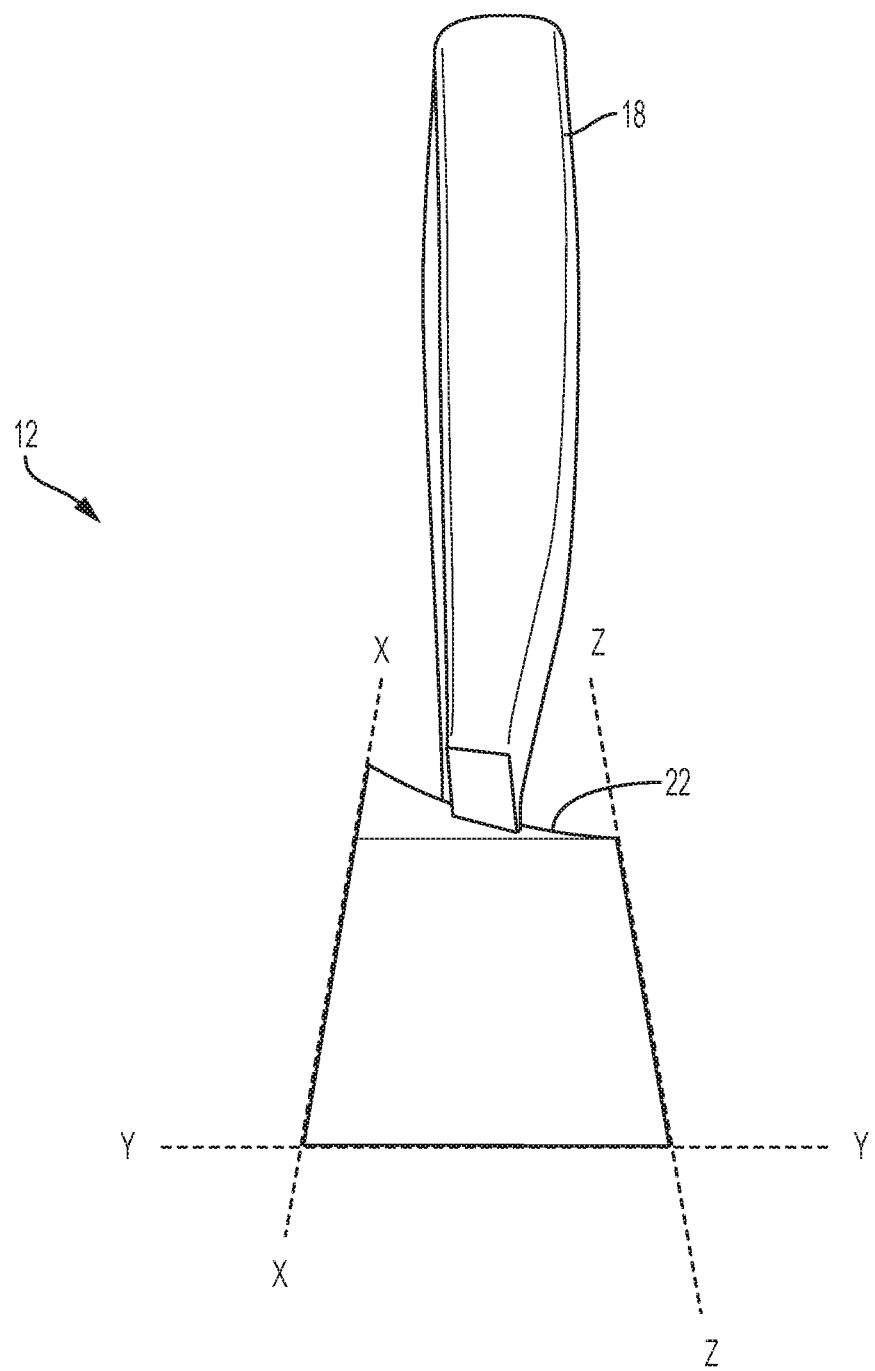
FIG. 8 is a perspective view of a donor bone graft prepared on a workstation according to the present invention.

Referring to FIG. 7, a third cutting gate 80 having a slot 82 formed therein for accepting a saw blade 78 may be positioned over graft 12 using a pair of bosses 86 and 88 at either end that are adapted to accept guide posts 48 and 50, respectively. Third cutting gate 80 is oriented to define a third cutting path that is angled slightly distally away from vertical so the newly formed rear face of graft 12 has a slight bevel and is wider toward the bottom side of graft 12 relative to meniscal horns 22 and 24. Third cutting gate 80 is also offset distally from posts 48 and 50 (and axis A-A of meniscal horns 22 and 24) so that the third cutting path is positioned to the rear side of posts 48 and 50 and on the other side of meniscal horns 22 and 24 from the first cutting path established by the first cutting path of first cutting gate 52. Saw blade 78 may then be applied through slot 82 to cut graft 12 along the third cutting path. Third cutting gate 80 may comprise first cutting gate 52 positioned on workstation 10 in a reversed orientation so that the offset of first cutting gate 52 is toward the back of workstation 10 and on the opposite side of meniscal horn 18. In this approach, the front and rear sides of first cutting gate 52 should be clearly marked so that first cutting gate 52 is appropriately positioned by a user when used as either first cutting gate 52 or third cutting gate 80. In addition, keying of posts 48 and 50 relative to bosses 86 and 88 (which may also be bosses of 56 and 58 of first cutting gate 52), can allow for reversal but not upside down attachment to posts 48 and 50. The width of the cut graft 12 will thus be twice the amount of offset of slot 52 relative to the axis of posts 48 and 50. In other words, an offset of 5 millimeters will produce graft 12 having an approximate width of 10 millimeters (not accounting for the slight taper of first cutting path). More specifically, as seen in FIG. 8, sawing donor graft 12 along first cutting path X-X, second cutting path Y-Y and third cutting path Z-Z results in a final graft 12 having a isosceles trapezoidal cross-section with meniscus 18 extending from the top side 22 of graft 12, which is narrower base of the isosceles trapezoid cross-sectional shape. First cutting path X-X and third cutting path Z-Z are both offset from vertical by about 5 degrees so that graft 12 tapers inwardly toward second cutting path Y-Y.

Figure 9:
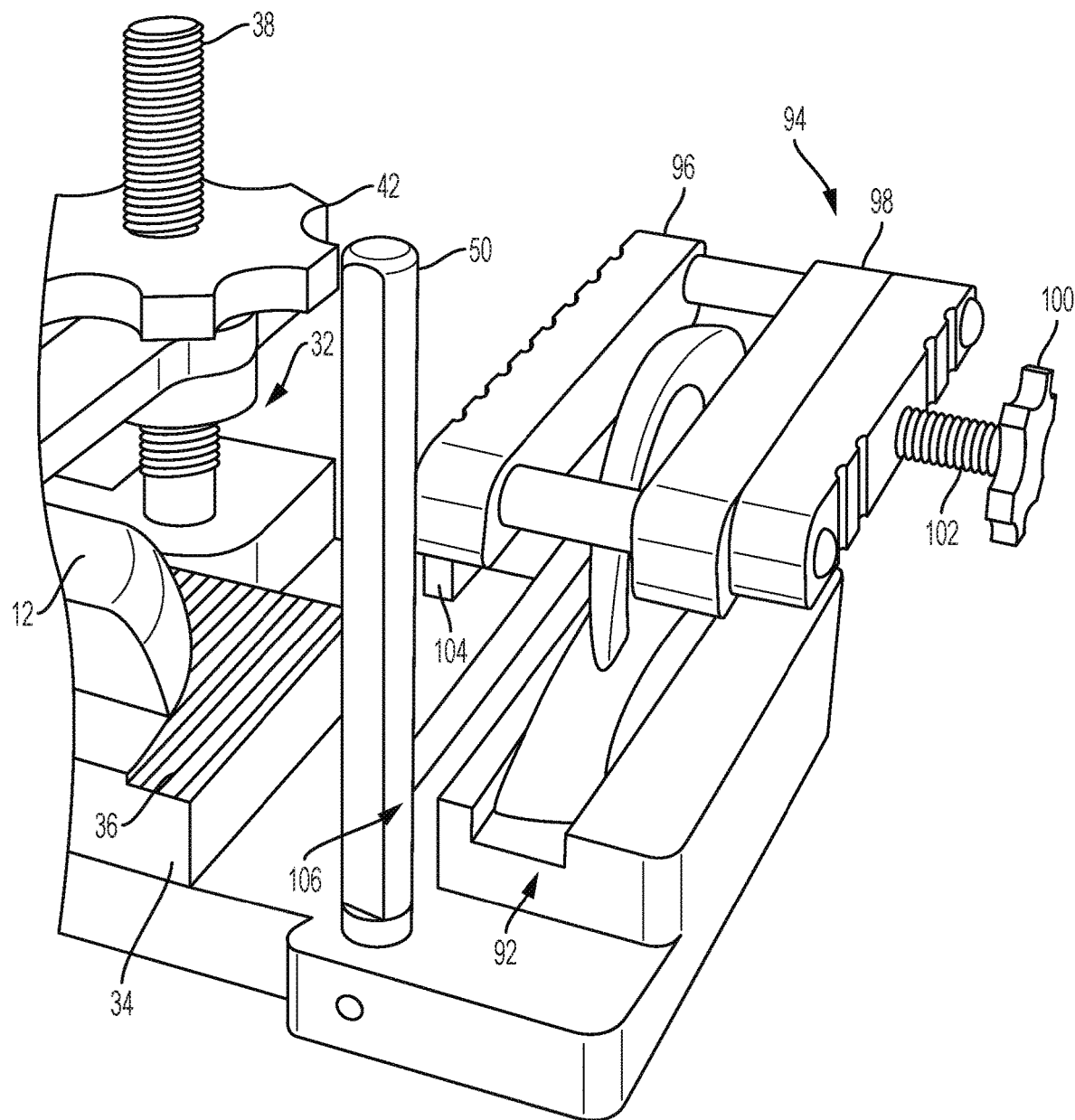
FIG. 9 is a perspective view of a workstation and graft clamp according to the present invention.
Figure 10:
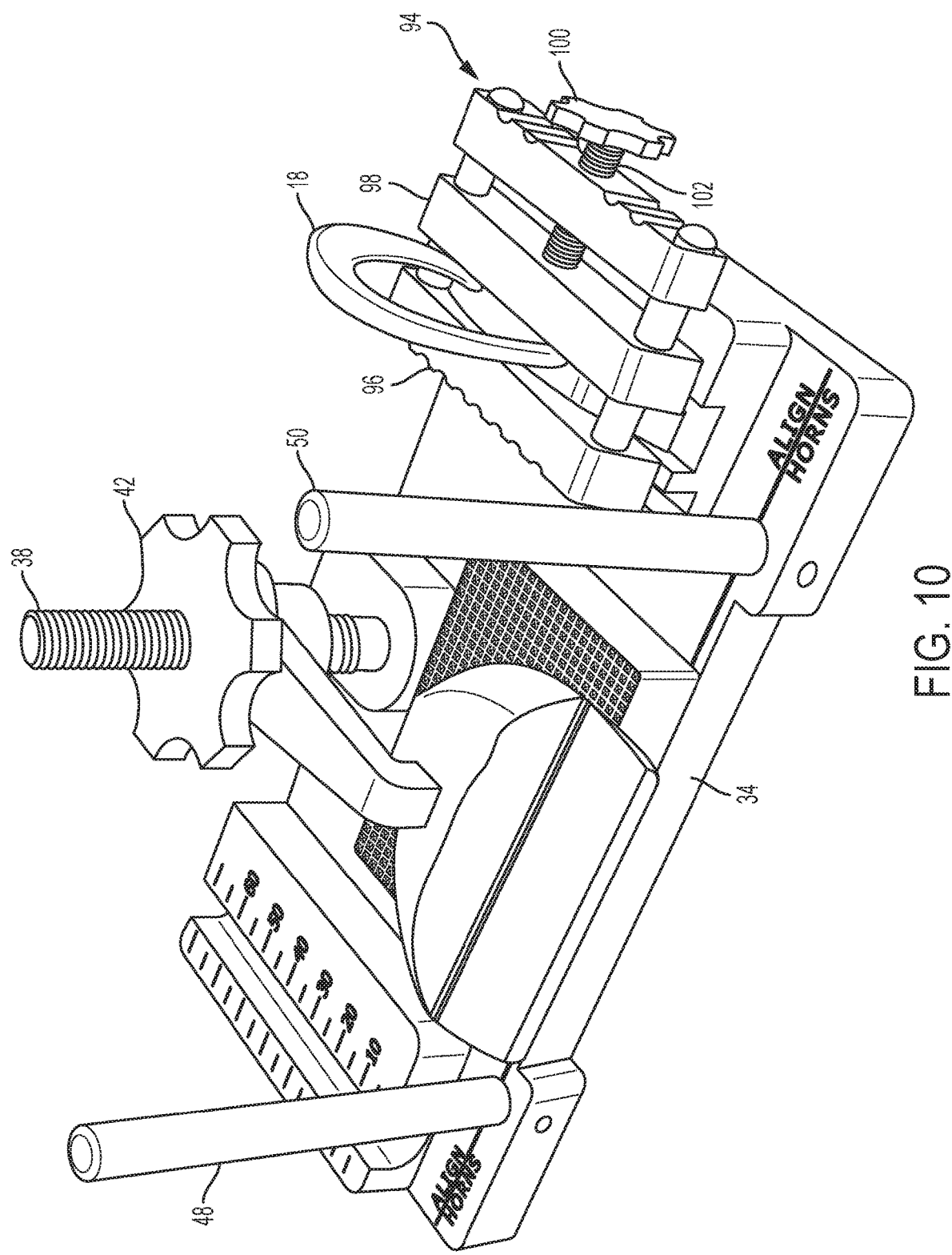
FIG. 10 is another perspective view of a workstation and graft clamp according to the present invention.

Referring to FIG. 9, base 30 further comprises a depth setting groove 92 that is dimensioned to accept trapezoidal graft 12 therein. Once trapezoidal graft 12 is positioned in groove 92, a graft clamp 94 may be fitted over graft 12. Graft clamp 94 comprises a fixed member 96 and an opposing moveable member 98 that can moved into and out of secure engagement with graft 12. As seen in FIG. 10, graft clamp 94 is positioned around graft 12 and seated onto workstation 10. Using an adjustment knob 100 having a threaded shaft 102 interconnected to moveable member. Groove 92 has a predetermined depth corresponding to the desired depth of graft 12 so that subsequent milling using graft clamp 94 as a milling guide will not remove more material from graft 12 than is needed to prepare graft 12 for implantation but will allow the appropriate radius to be formed in the bottom of graft 12. For example, 5 millimeter should extend below graft clamp 94 so that subsequent machining provides the appropriately shaped graft 12. Fixed member 96 may include a protrusion 104 that seats in an alignment groove 106 that extends along workstation 10 parallel to depth setting groove 92. If graft 12 is fully seated in groove 92 and graft clamp 94 affixed thereto so that graft clamp 94 is resting on workstation 10, graft clamp 94 can be used as a machining guide to ensure that graft 12 is precisely machined into the desired dimensions prior to implantation. Both contacting portions of graft clamp 94 may have checkered, textured or spiked surfaces for using suitable approaches, such as, milling with a CNC machine. The exact pattern of the checkering or texturing is unimportant as long as the pattern sufficiently fixes the position of the nearly completed donor part in the graft clamp 94 so that it does not move with respect graft clamp 94 during subsequent operations that create the final rounded edge of graft 12 prior to implantation.

Figure 11:
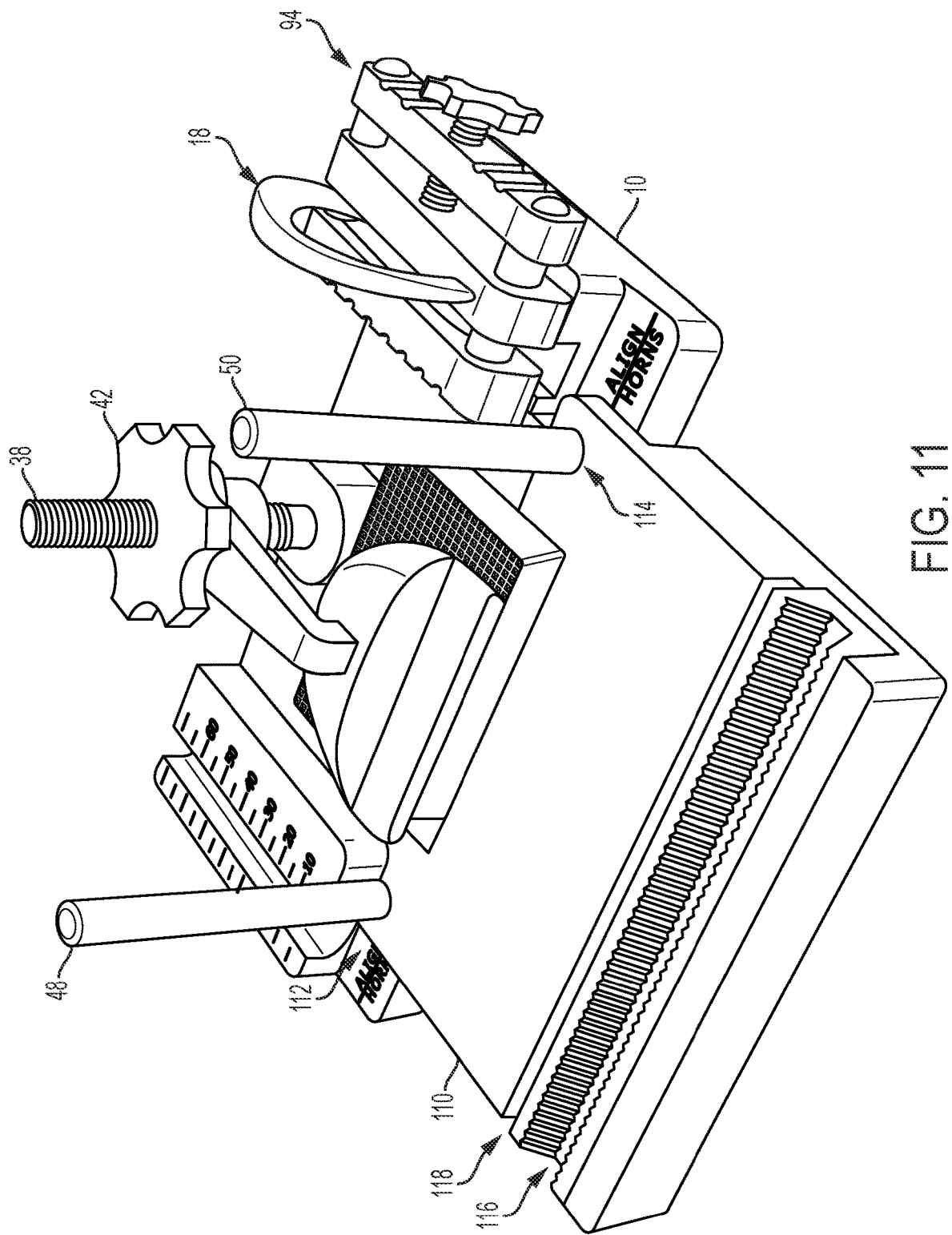
FIG. 11 is a perspective view of a workstation and a first shaver according to the present invention.
Figure 12:
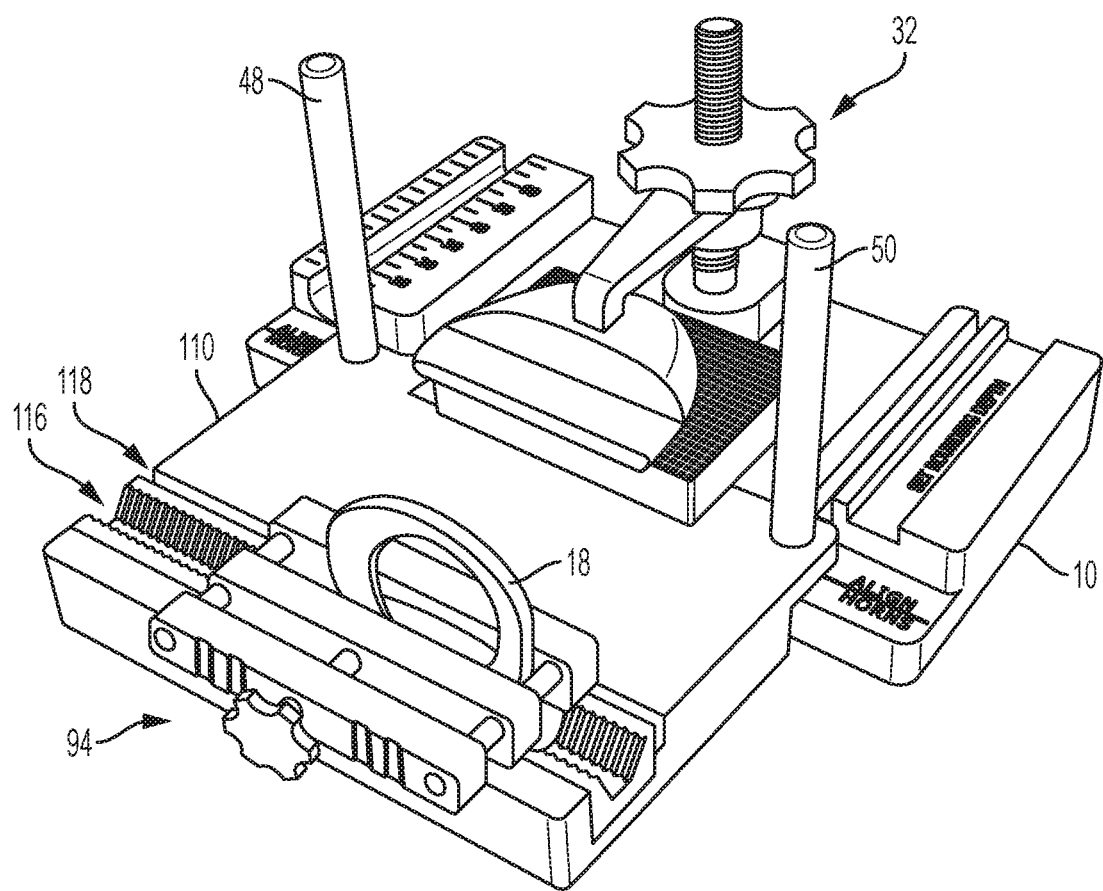
FIG. 12 is another perspective view of a workstation and a first shaver according to the present invention.
Figure 13:
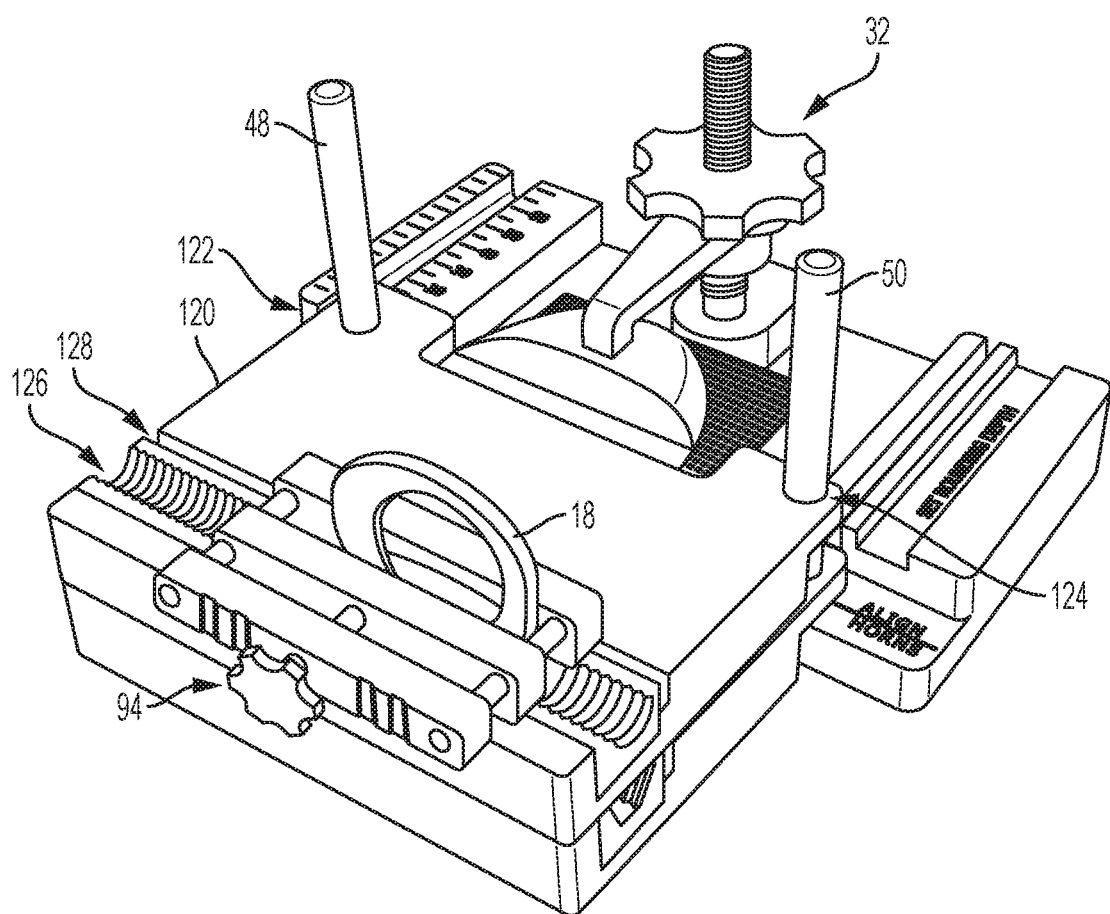
FIG. 13 is a perspective view of a workstation and a second shaver according to the present invention.

Referring to FIG. 11, a first shaver 110 may be secured to workstation 10 by positioning a pair of opposing holes 112 and 114 formed in first shaver 110 over guide posts 48 and 50. Graft clamp 94 may then be placed against first shaver 110 so that the bottom of graft 12 is in engagement with a shaving channel 116 of first shaver 110. An alignment channel 118 that accepts protrusion 104 extends parallel to shaving channel to ensure graft 12 is moved precisely longitudinally along shaving channel 116. Graft clamp 94 may then be moved along the surface of first shaver 110 so that shaving channel 116 removes material from graft 12, as seen in FIG. 12. As explained above, graft clamp 94 thus acts as a machining guide and ensures that the appropriate amount of material is removed from graft 12 to precisely form the desired dimensions of graft 12. First shaver 110 is preferably used to finish to bevel the underside of graft 12 to produce a preliminary taper on the base of graft 12 to facilitate subsequent operations. Once shaving is completed, a second shaver 120 may be secured to workstation 10 by positioning a pair of opposing holes 122 and 124 formed in second shaver 120 over guide posts 48 and 50, as seen in FIG. 13. Graft clamp 94 may then be used to position the bottom of graft 12 in a second shaving channel 126 with protrusion 104 in an alignment channel 128. Clamp 94 may then be used to move graft 12 along second shaver 120 so that second shaving channel 126 removes the appropriate material from the bottom of graft 12 to form the desired radius of curvature for the bottom of graft 12. Once second shaver 120 has been used, graft 12 is removed from graft clamp 94.

Figure 14:
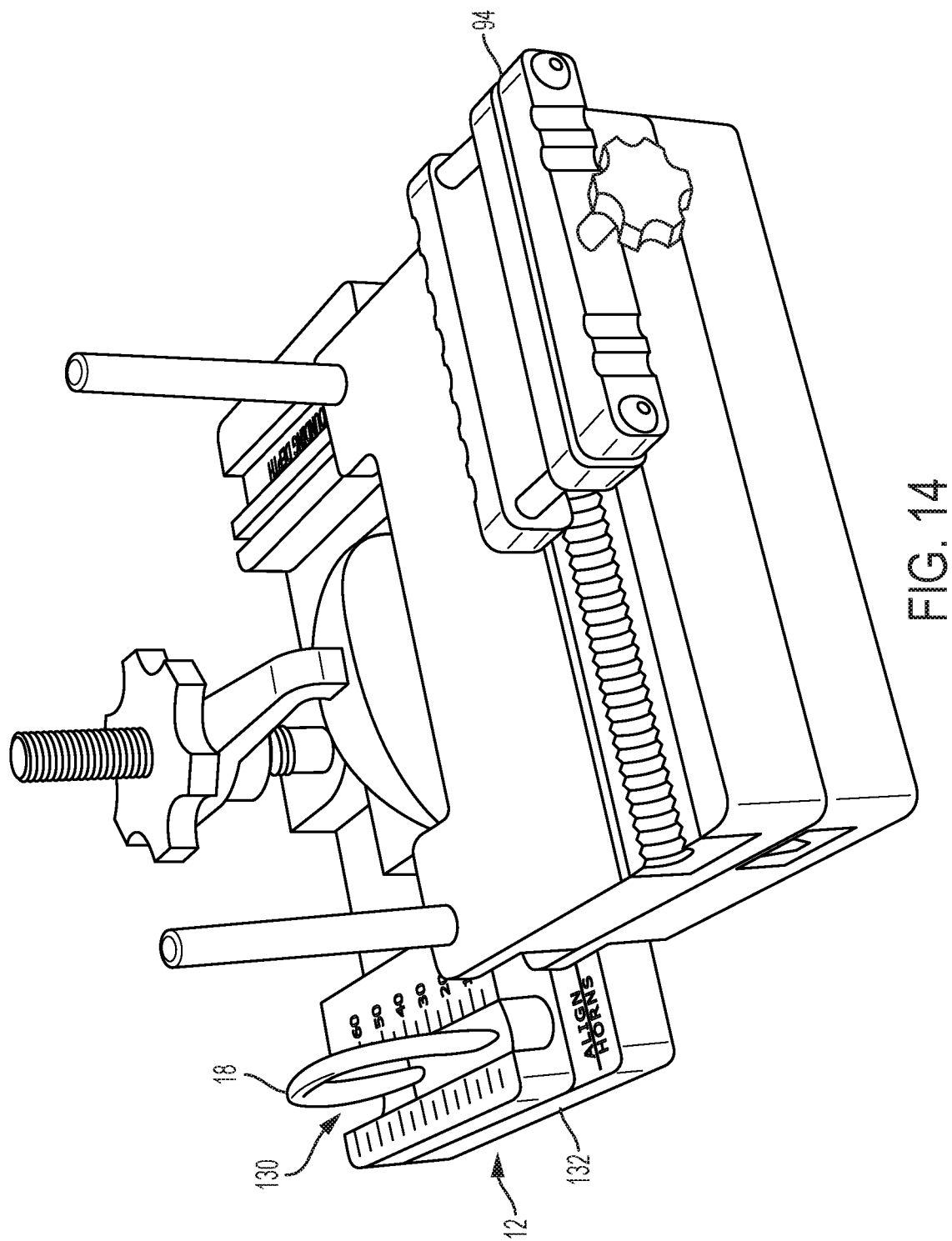
FIG. 14 is a perspective view of another aspect of workstation according to the present invention.

Referring to FIG. 14, workstation 10 includes a trial slot 130 is dimensioned to accept graft 12 after it has been shaved by first shaver 110 and second shaver 120. More particularly, trial slot 130 has a bottom 132 with a radius corresponding to the newly formed radius of graft 12. Trial slot 130 is associated with indicia 134 on workstation 12 that is indexed to allow for an easy visual determination of the length of graft 12. The length of graft 12 may be trimmed using trial slot 120 to the appropriate length for implantation so that the meniscal horns 22 and 24 are located in the appropriate position when graft 12 is implanted into a tibia prepared according to the present invention, as explained below.

Workstation 10 and its associated components discussed above may be made from any suitable material, such as stainless steel (e.g., 17-4PH stainless steel or NITRONIC 60). Any numbers or lettering can be made using a suitable marking method, such as laser etching. Components may also be passivated after laser etching according to ASTM A967 or ASM-QQ-P-35.

Figure 15:
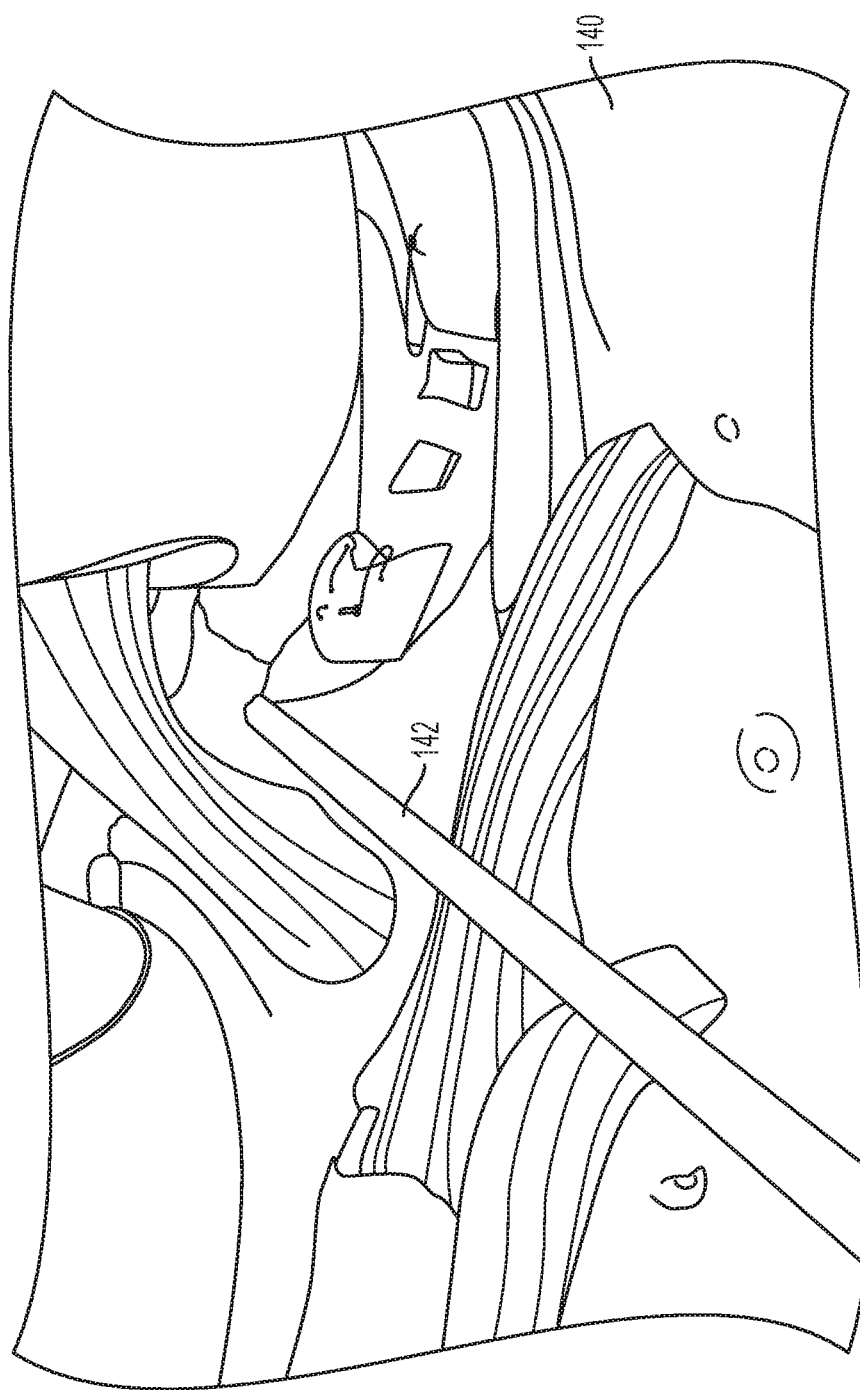
FIG. 15 is a perspective view of a tibia and meniscus to be repaired with a bone graft according to the present invention.
Figure 16:
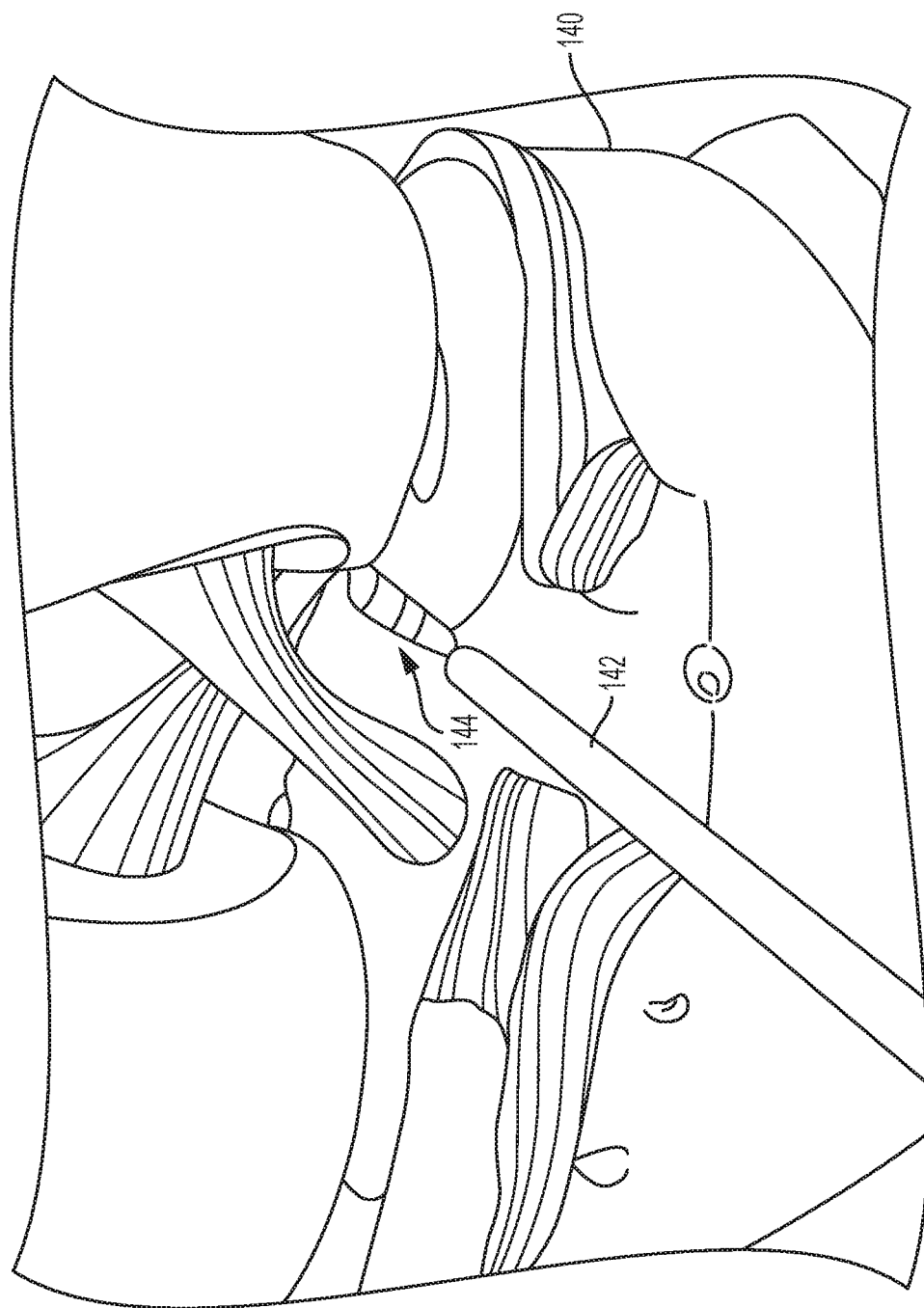
FIG. 16 is another perspective view of a tibia and meniscus to be repaired with a bond graft according to the present invention

Referring to FIG. 15, the tibia 140 of a patient may be prepared by performing a menisectomy and removing any debris associated with the meniscus to be replaced, such as by using a shaver 142. As seen in FIG. 16, a notch 144 is formed in the tibial eminence.

Figure 17:
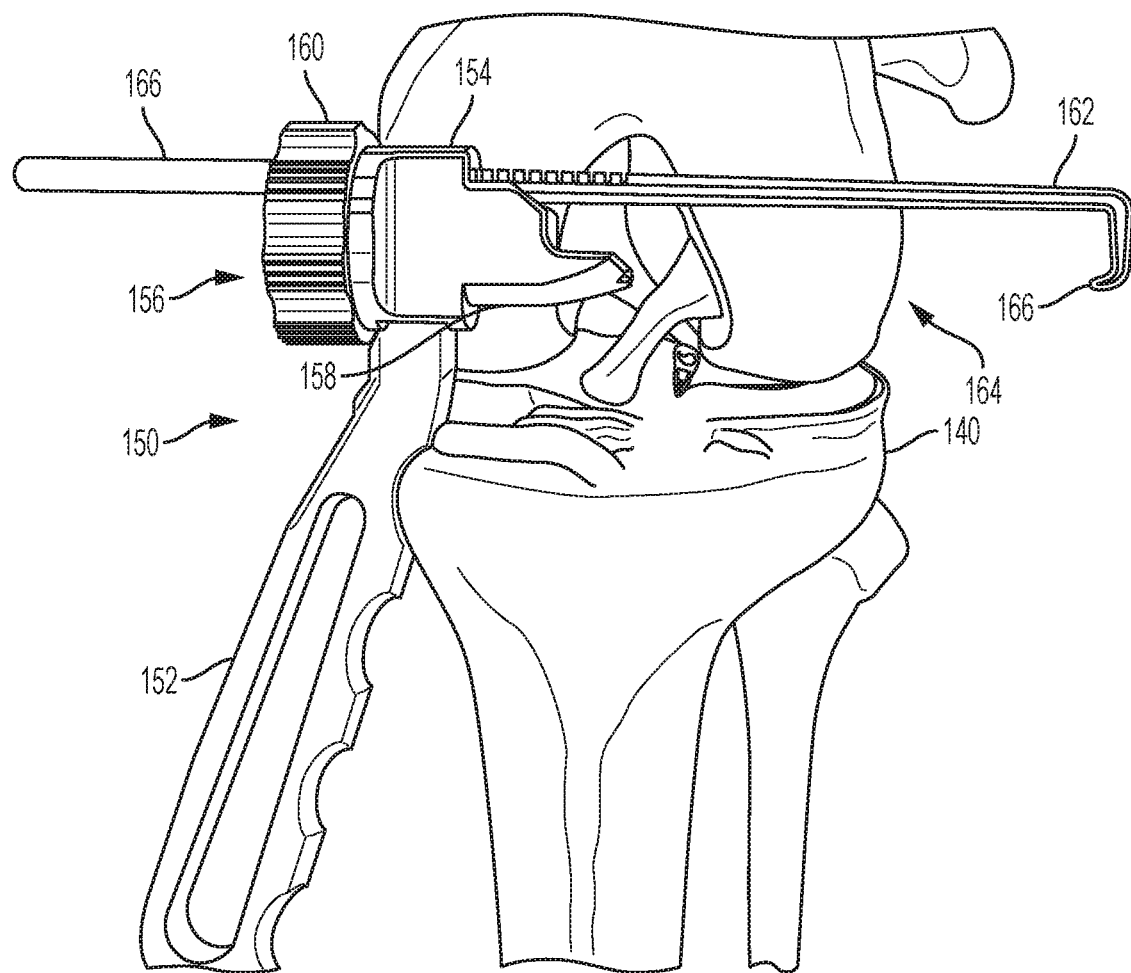
FIG. 17 is a perspective view of drill guide according to the present invention.
Figure 18:
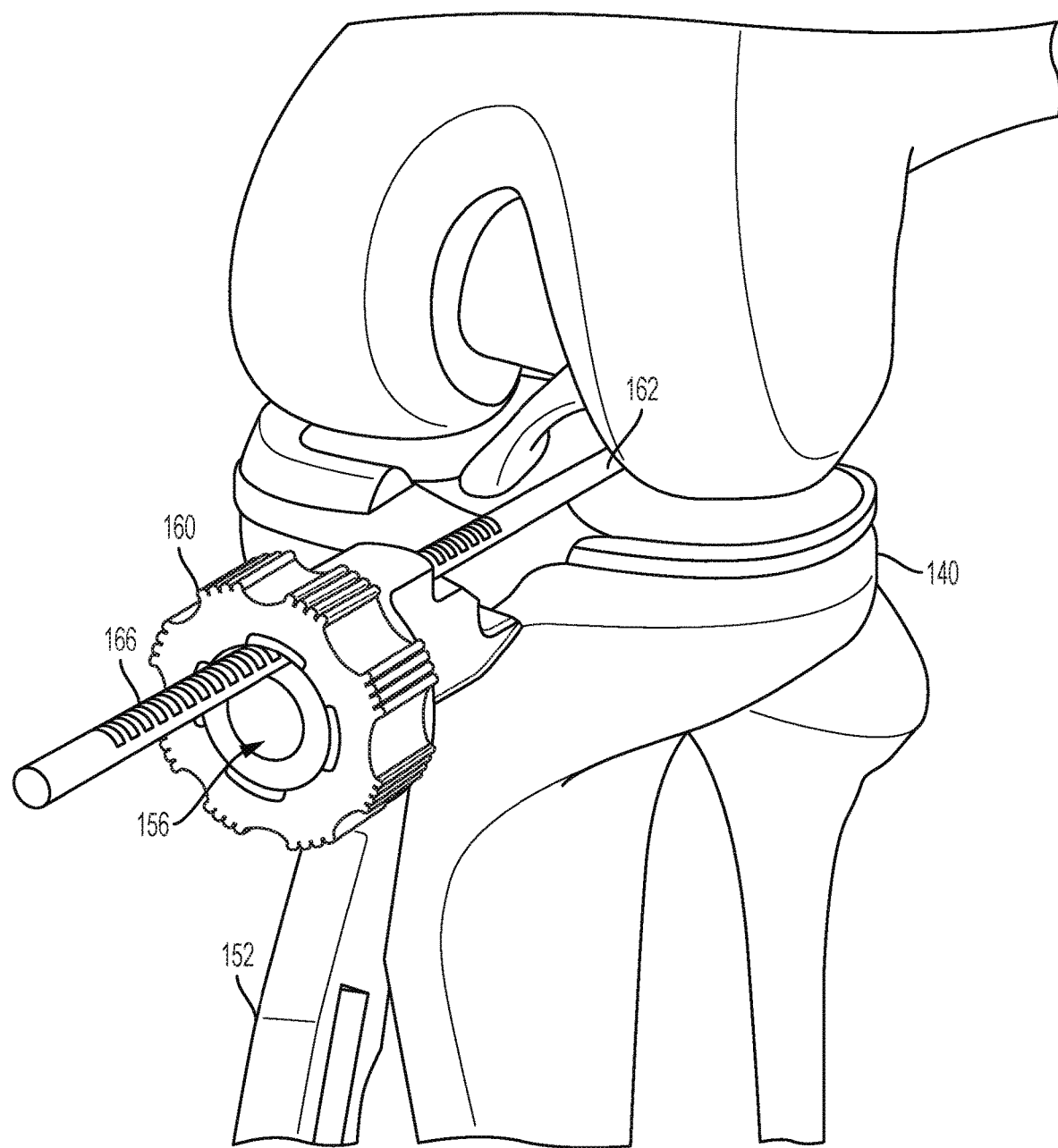
FIG. 18 is a perspective view of drill guide and tibia according to the present invention.

Referring to FIG. 17, the invention further comprises a drill guide 150 having a handle 152 extending from a main body 154 having a throughbore 156 and a spacer 158 for engaging and spacing main body 154 a predetermined distance from a tibia 140. An adjustment wheel 160 is positioned around throughbore 156 and interconnected to a hook beam 162 that extends through main body 160 above throughbore 156. Hook beam 162 extends outwardly from drill guide 150 to define an adjustable tibia receiving space 164 between a curved end 166 of hook beam 162 and spacer 158. Hook beam 162 has multi-start threads 166 formed therein that interconnect to threads on the inside of adjustment wheel 160 so that hook beam 162 can be extended over tibia 140 and then retracted to secure tibia 140 in tibia receiving space 164 between curved end 166 of hook beam 162 and spacer 158 of main body 154 by turning adjustment wheel 160, as seen in FIG. 18. Preferably, adjustment wheel 160 has multi-start threads so that hook beam 162 is advanced quickly while reducing the risk of overtightening due to the reduced torque that is possible. Hook beam 162 is calibrated so that the distance from its proximal end to curved end 166 is known and thus, when connected to a tibia, provides a gauge so that the depth of subsequent drilling operation can be coordinated to prevent overdrilling, such as by allowing for a safe stopping distance of about 5 millimeters.

Figure 19:
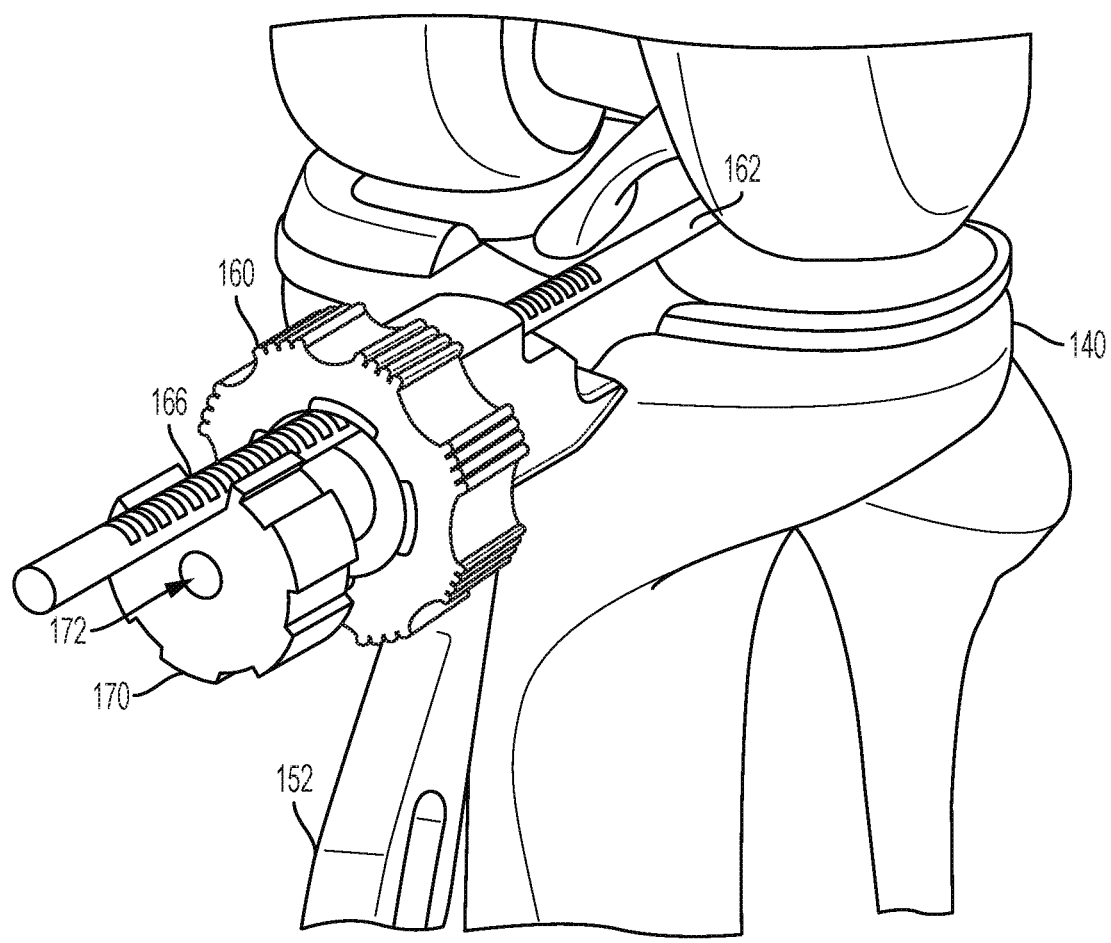
FIG. 19 is a perspective view of drill guide with a pilot drill guide according to the present invention.

Referring to FIG. 19, a pilot guide 170 having a narrow through bore 172 that is dimensioned to receive a pilot drill bit 174 may be inserted into throughbore 156 of drill guide 150 and locked into position via rotation of pilot guide 170 so that a cam on pilot guide 170 interlocks with the underside of hook beam 162. Pilot guide 170 should preferably contact tibia 140 securely to prevent drill bit slippage across the surface of tibia 140.

Figure 20:
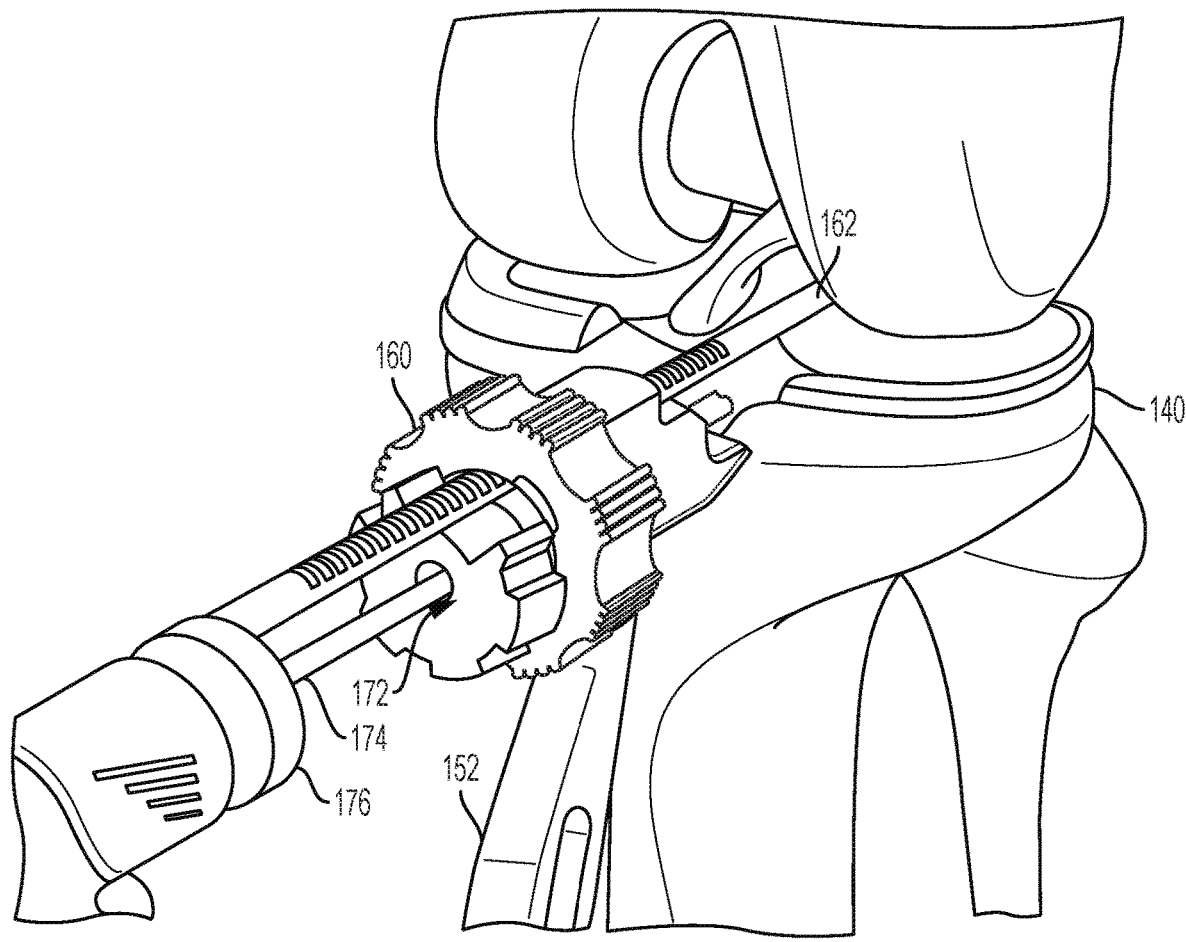
FIG. 20 is a perspective view of drill guide with a pilot drill guide and pilot drill bit according to the present invention.

Referring to FIG. 20, a pilot drill bit 174 may then be passed through the narrow throughbore 172 of pilot guide 170 and used to drill a pilot hole in tibia 140. Pilot drill bit 174 is associated with a drill stop 176 that will engages the proximal end of hook beam 162 when bit 174 traverses a predetermined distance into tibia 140 and thus prevent over insertion of pilot drill bit 174 into tibia 140. Preferably, drill stop 176 allows for at least about 5 millimeters of spacing between the end of pilot drill bit 174 and curved end 166 of hook beam 162 to ensure that drilling does not extend through the distal side of tibia where damage can occur to any of the major blood vessels in that area. It should be recognized the appropriate positioning of drill stop 176 will depend on various factors, such as the length of hook beam 162, and can be calculated and established in advance based on the particular circumstances. In other words, the lengths of hook beam 162 and drill bit 174 are interrelated and correlated to each other to ensure against overdrilling without the need for a surgeon to take depth measurements during drilling operations.

Figure 21:
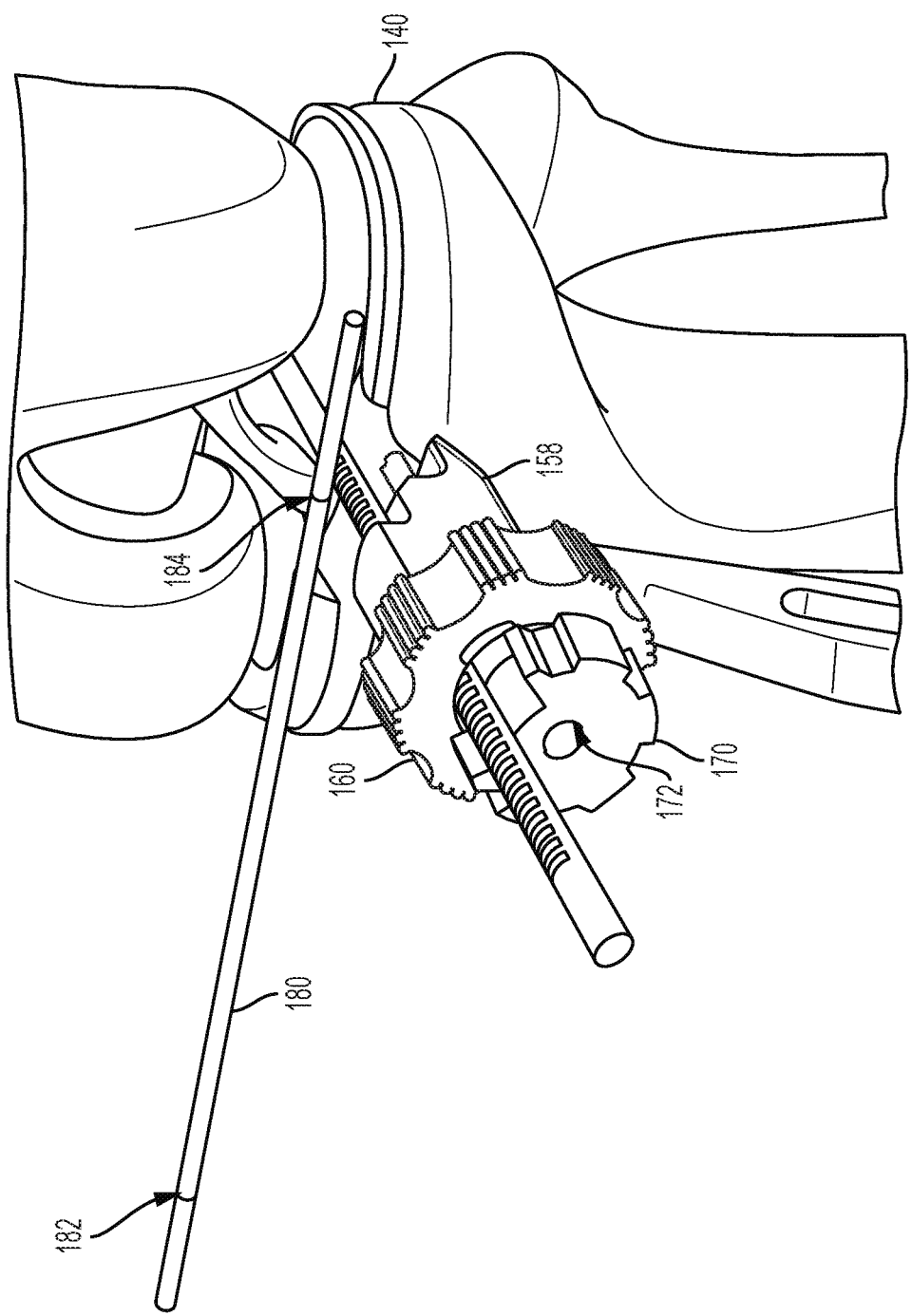
FIG. 21 is a perspective view of drill guide with a drill guide pin according to the present invention.
Figure 22:
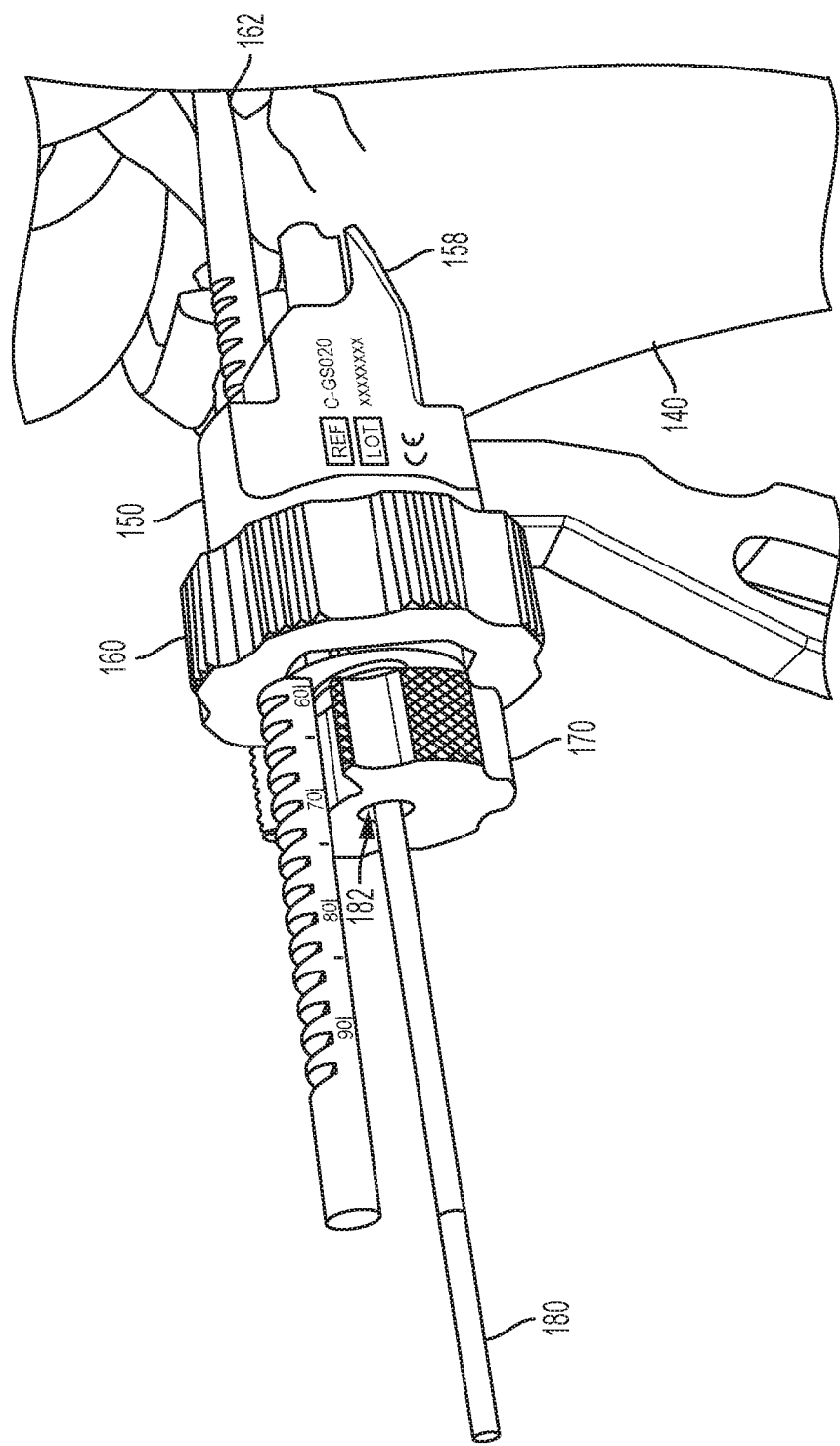
FIG. 22 is a perspective view of drill guide with a guide pin inserted into a tibia according to the present invention.

Referring to FIGS. 21 and 22, once a pilot hole has been formed in tibia 140, a blunt guide pin 180 having indexing marks 182 and 184 may be inserted into the pilot hole by inserting guide pin 180 through narrow throughbore 172 of pilot guide 170. Indexing of guide pin 180 may be used to confirm that the pilot hole has been drilled to an appropriate depth as one indexing mark 182 or 184 should align with the proximate end of hook beam when properly inserted to the appropriate depth into the pilot hole. Guide pin 180 is blunted to ensure that any frictional engagement during subsequent drilling does not advance guide pin 180 further into tibia 140. Pilot guide 170 may then be unlocked from drill guide 150 and removed, as seen in FIG. 23, leaving guide pin 180 in place.

Figure 24:
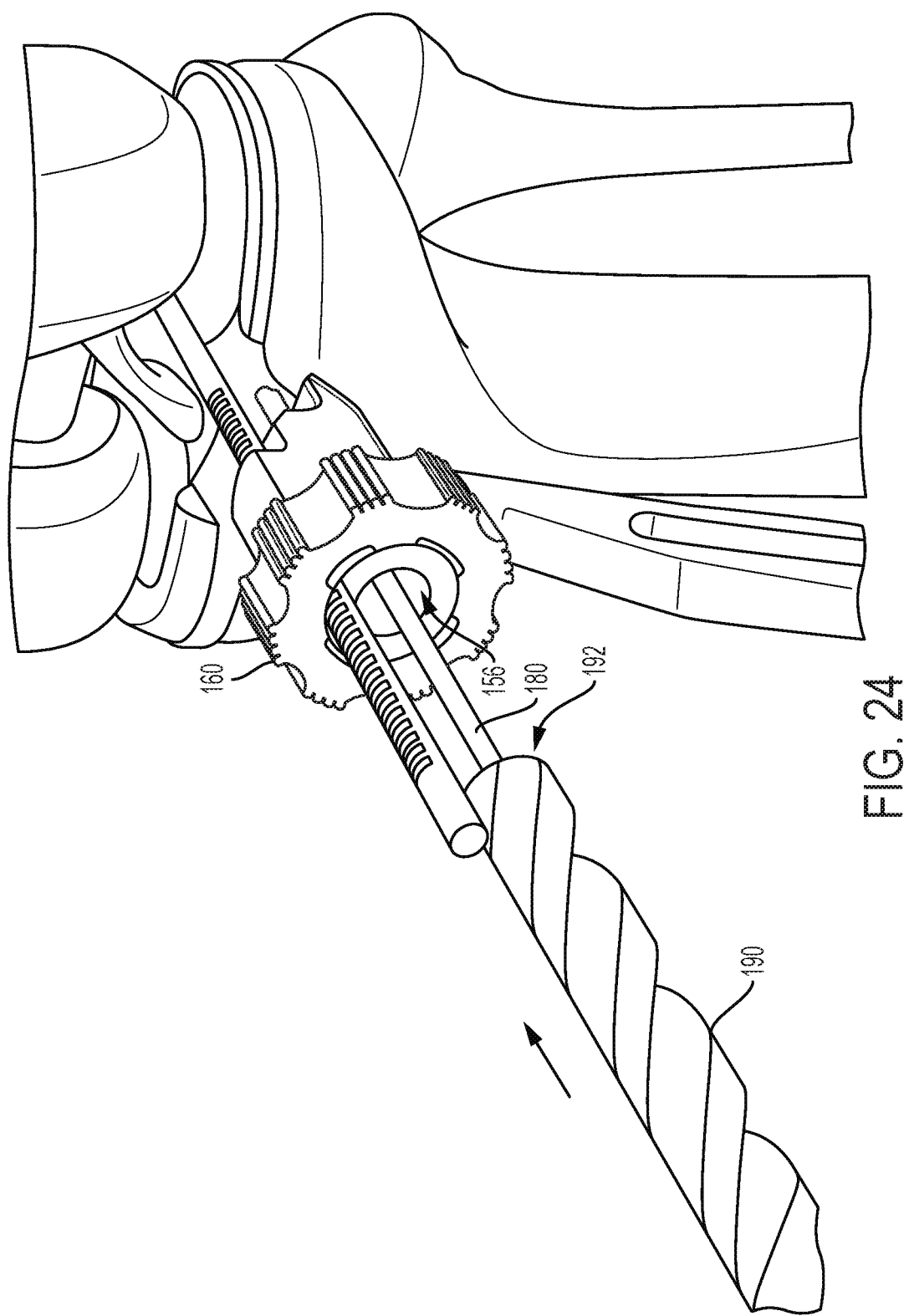
FIG. 24 is a perspective view of a cannulated drill bit being inserted over a guide pin into a tibia according to the present invention.
Figure 25:
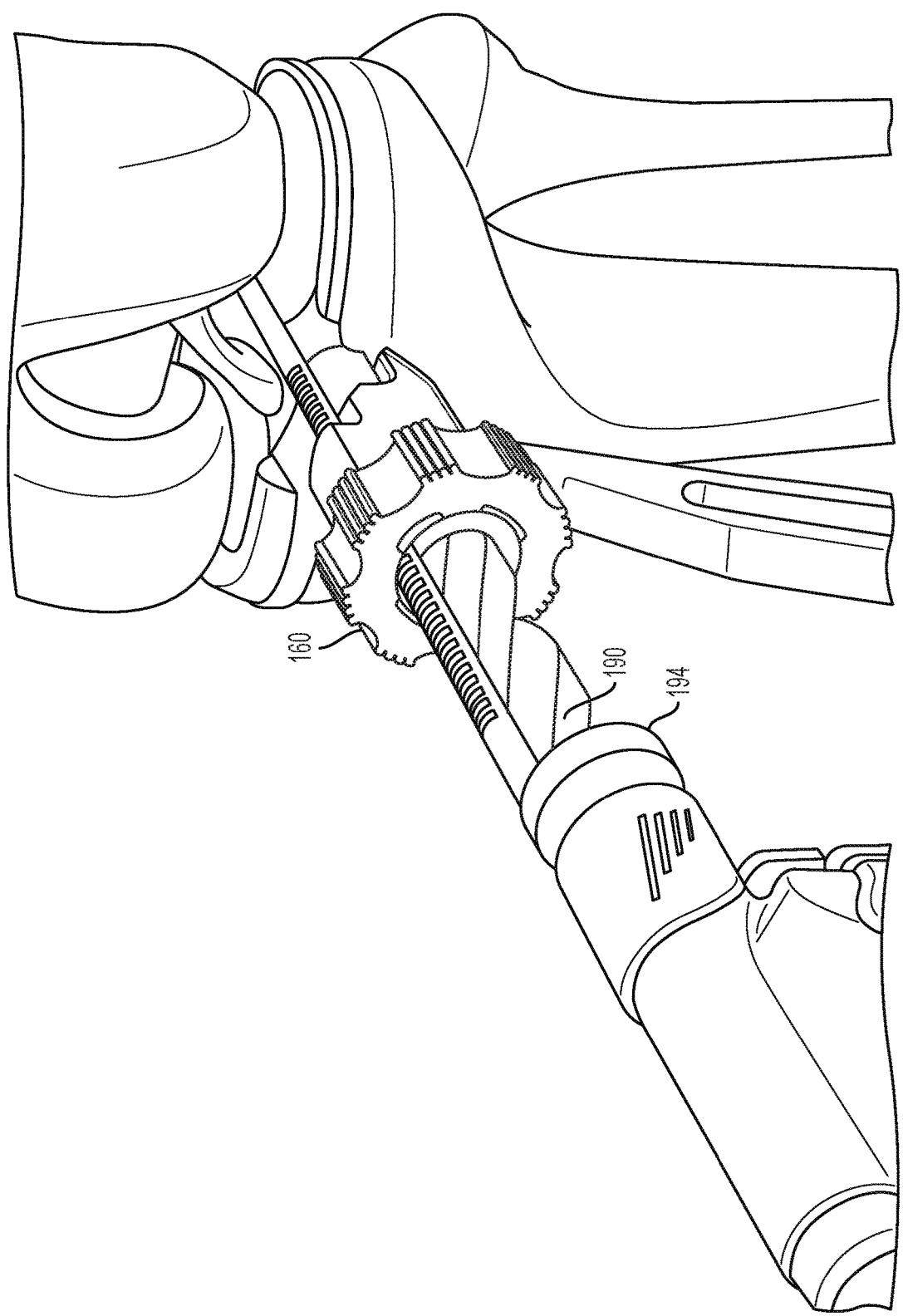
FIG. 25 is a perspective view of a cannulated drill bit fully inserted over a guide pin into a tibia according to the present invention.

Referring to FIG. 24, a cannulated drill bit 190 having a throughbore 192 for receiving guide pin 180 may be inserted into throughbore 156 of drill guide 150 with guide pin 180 is received in throughbore 192 of drill bit 190. Drill bit 190 may then be used to drill a larger hole in tibia 140, as seen in FIG. 25. Drill bit 190 preferably includes a drill stop 194 that is positioned to engage the proximate end of hook beam 162 of drill guide 150 when drill bit 190 has been inserted an appropriate depth to, once again, prevent over-insertion of drill bit 190. It should be recognized the appropriate positioning of drill stop 194 will depend on various pre-established factors, such as the length of hook beam 162 and desired depth of the hole in tibia, and can be calculated and established in advance based on the particular circumstances. Once the hole 196 is drilled, drill guide 150 and all components are removed from site.

Figure 26:
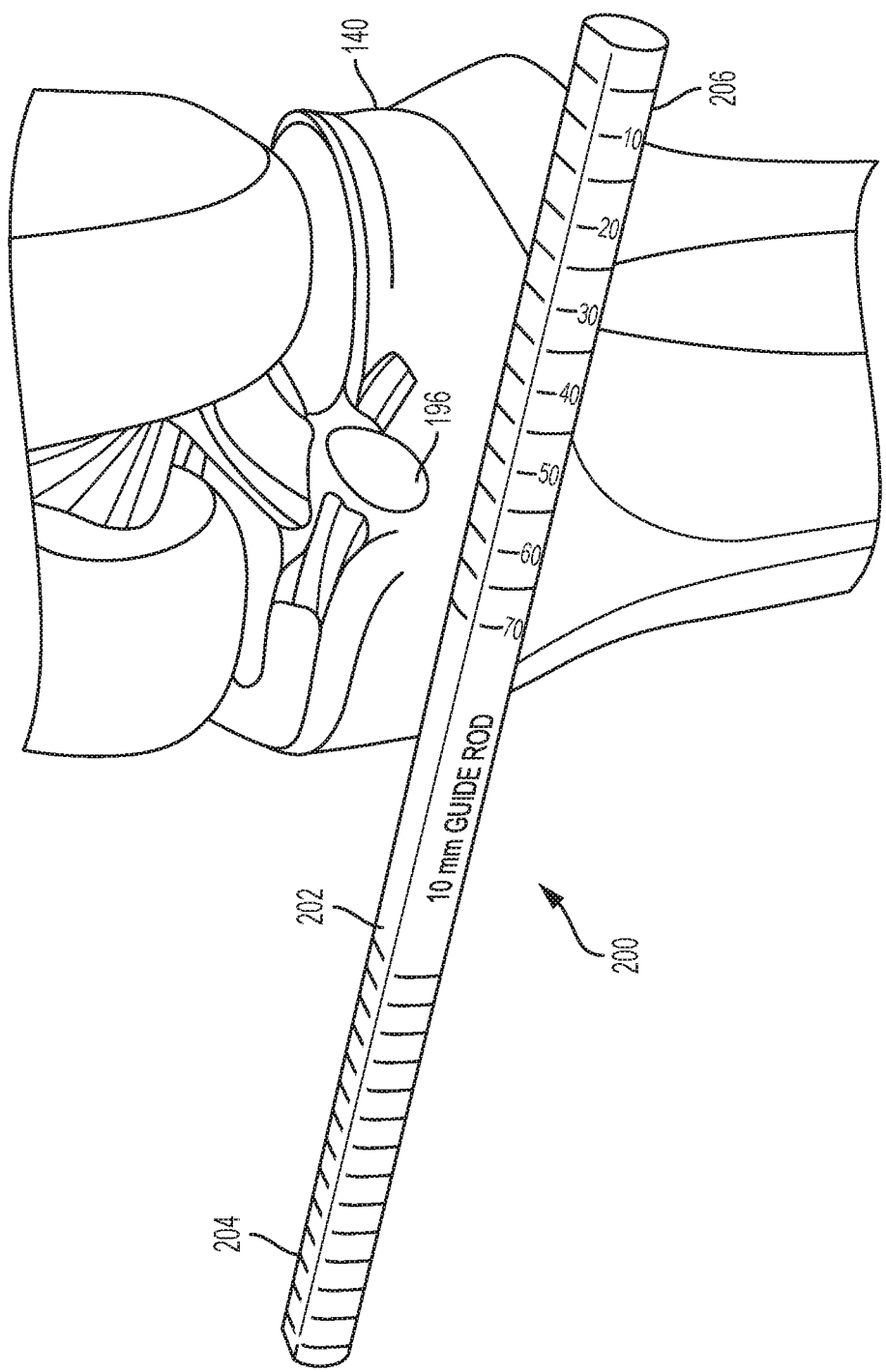
FIG. 26 is a perspective view of a guide rod according to the present invention.
Figure 27:
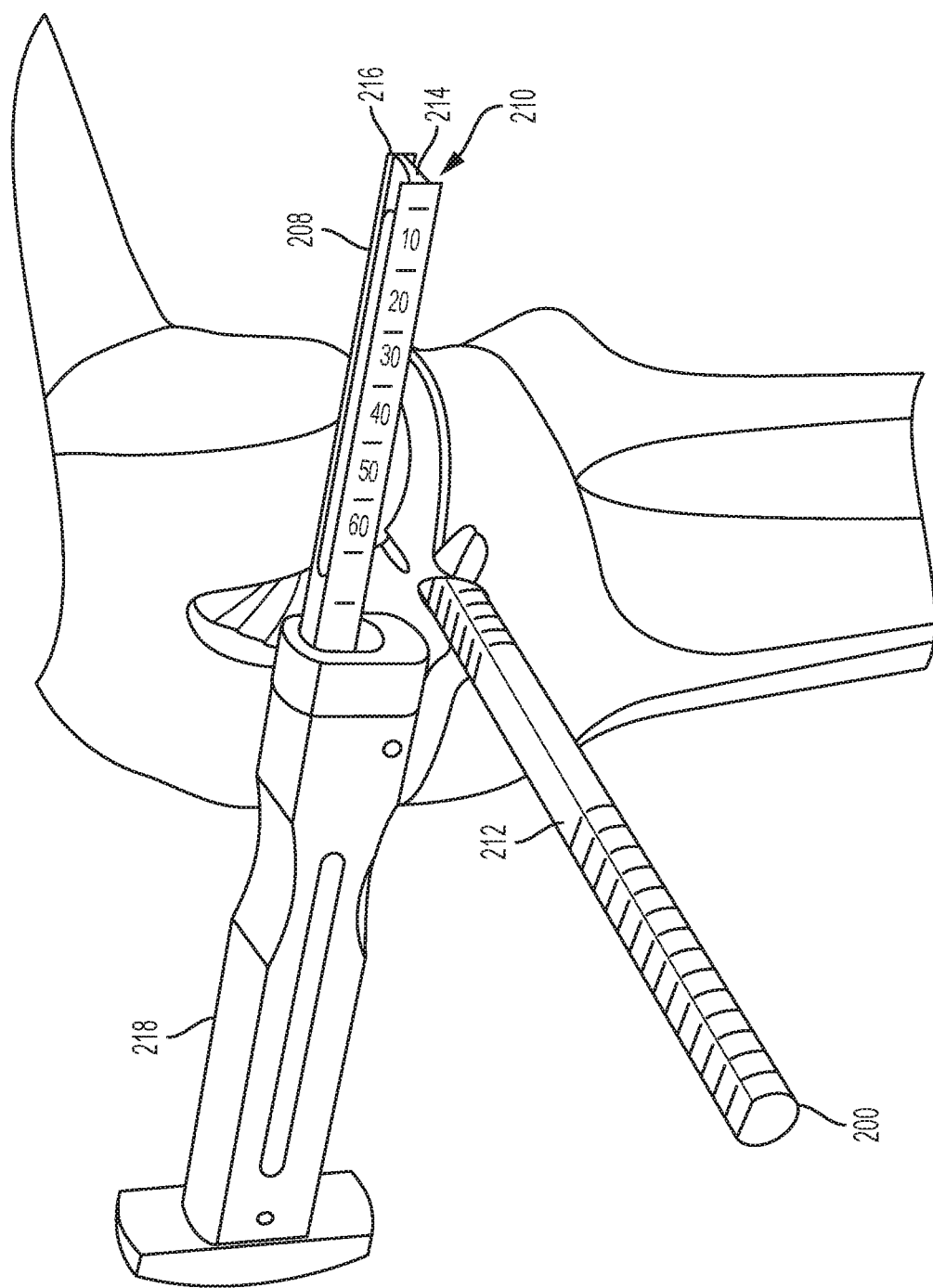
FIG. 27 is a perspective view of a chisel and a guide rod inserted into a tibia according to the present invention.
Figure 28:
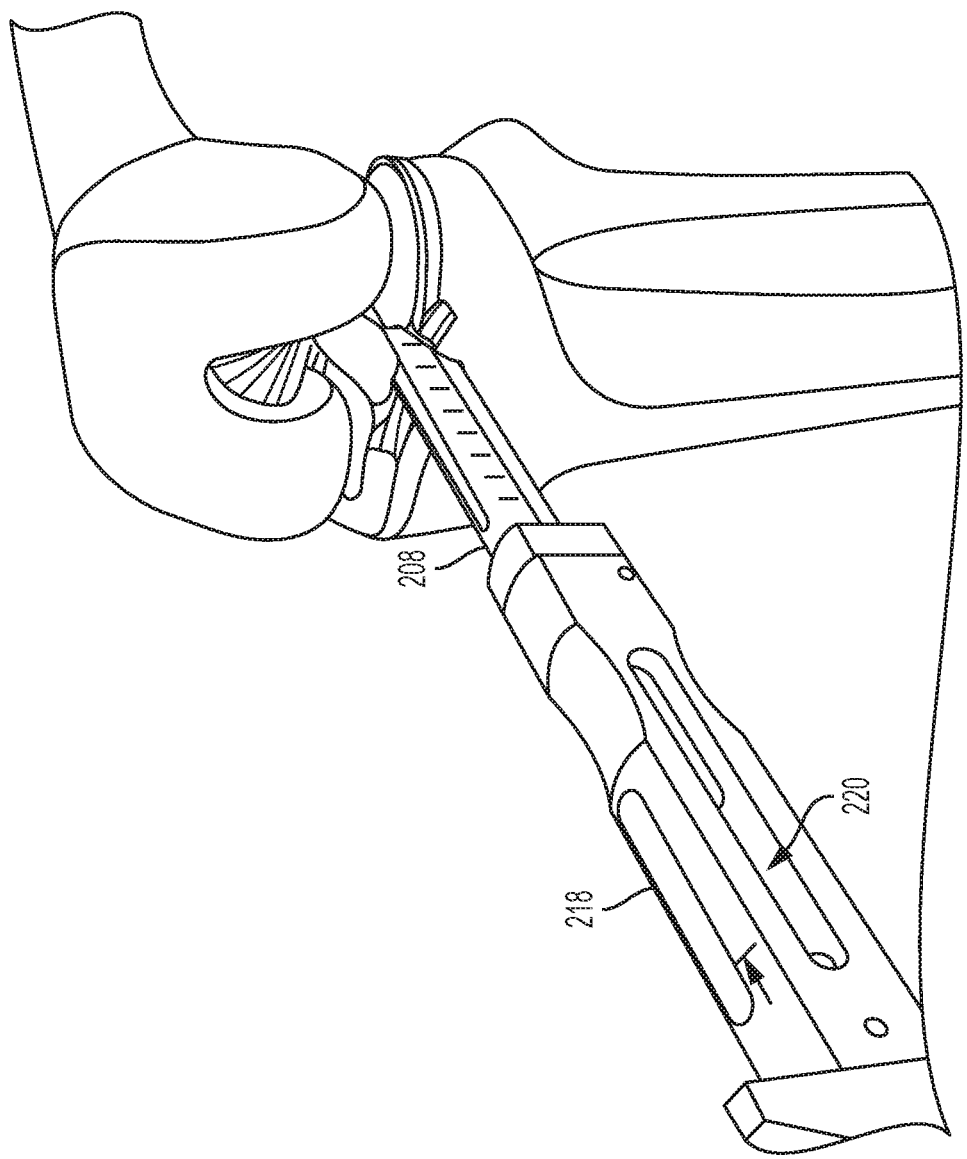
FIG. 28 is a perspective view of a chisel being inserted into a tibia using a guide rod according to the present invention.
Figure 29:
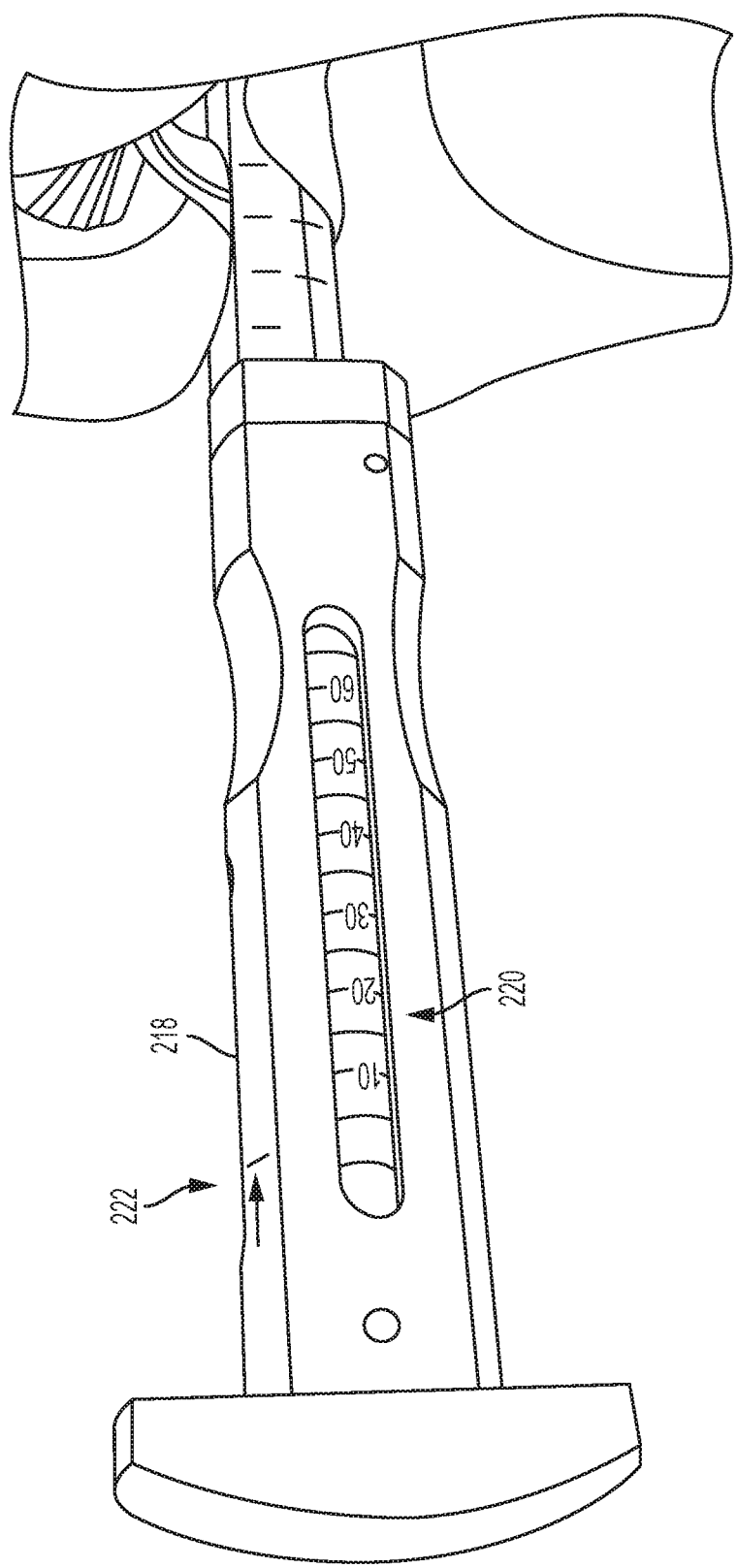
FIG. 29 is a perspective view of a chisel fully inserted into a tibia according to the present invention.

Referring to FIG. 26, a guide rod 200 comprising a shaft 202 having a first set of indexing at one end 204 at a second set of indexing at the opposing end 206 may be inserted into hole 196 in tibia 140. As seen in FIG. 27, guide rod 200 acts as a guide for a chisel 208 having a lower channel 210 dimensioned to slide along the upper surface 212 of guide rod 200 and a pair of opposing blades 214 and 216 positioned above the lower channel 210 to remove bone from tibia 140 along the sides of hole 196 to match the profile of graft 12. Guide rod 200 may incorporate a flat along its upper surface upon which a corresponding horizontal blade element of chisel 208 may be located in order to prevent the entrapment of bone fragments that could potentially cause chisel 208 and guide rod 200 to jam. Guide rod 200 may include indicia thereon to ensure that it is properly oriented when inserted into tibia 140, e.g., a legend such as "THIS SIDE UP" may be used. Indexing on ends of guide rod 200 indicate the distance from the respective ends of guide rod 20, and thus indicate the depth of hole 196 and the distance that chisel 208 has travelled along guide rod 200 into hole 196. Referring to FIG. 28, chisel 208 has a handle 218 with a window 220 formed therein so that indexing of guide rod 200 is clearly visible therethrough. Chisel 208 may be slidingly engaged over guide rod 200 and driven into tibia 140 to enlarge and shape hole 196 in tibia 140. As seen in FIG. 29, chisel 208 contains a stop 222 and associated indicia (such as a "STOP" line) on handle 218 that indicates, via movement of guide rod 200 inside window 220, how far to drive chisel 208 into hole 196. As explained above with respect to hook beam 162, a safe depth of hole 196 can be ensured by stopping the progress of bone removal when an inserted tool reaches an appropriate depth by using a gauge that is positioned in the hole 196 and used to stop the progress of the tool, such as stop 222 on the inside of chisel 208 that is reached when chisel 208 advances over guide rod 200, which acts the appropriate depth gauge. Once chiseling is complete, chisel 208 and guide rod 200 may be removed from hole 196.

Figure 30:
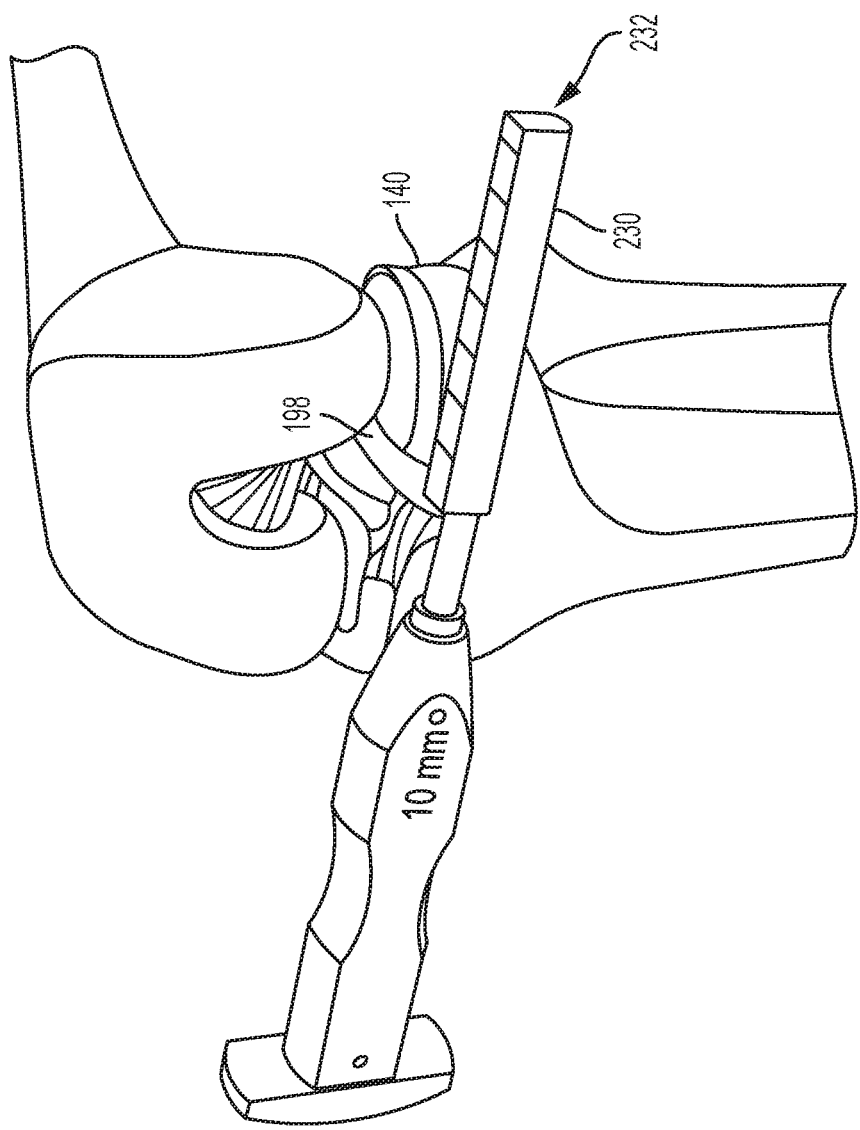
FIG. 30 is a perspective view of a rasp according to the present invention.
Figure 31:
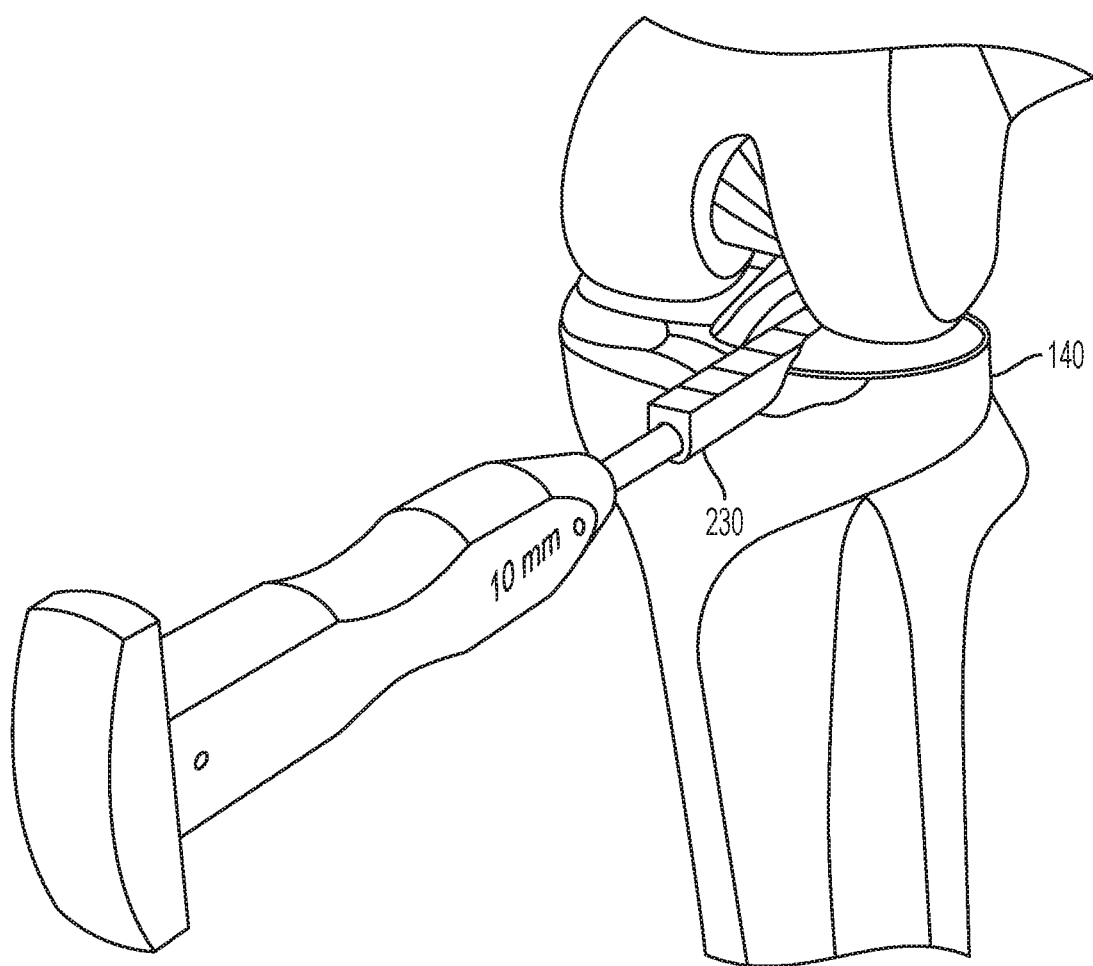
FIG. 31 is a perspective view of a rasp inserted in to a tibia according to the present invention.

Referring to FIG. 30, a rasp 230 having a U-shaped cross-section 232 corresponding to the profile of graft 12 may be inserted into hole 198 of tibia 140 if hole 198 does not have exactly the same profile as graft 12. Rasp 230 is used to remove material from hole 198 so that rasp 230 has the predetermined shape and dimensions of graft 12 when prepared using workstation 10 as explained above, as seen in FIG. 31. It should be recognized that the shape and dimensions of rasp 230 are selected to correspond to the shape and dimensions of graft 12 one appropriately cut and shaved using workstation 10, and vice versa.

Figure 32:
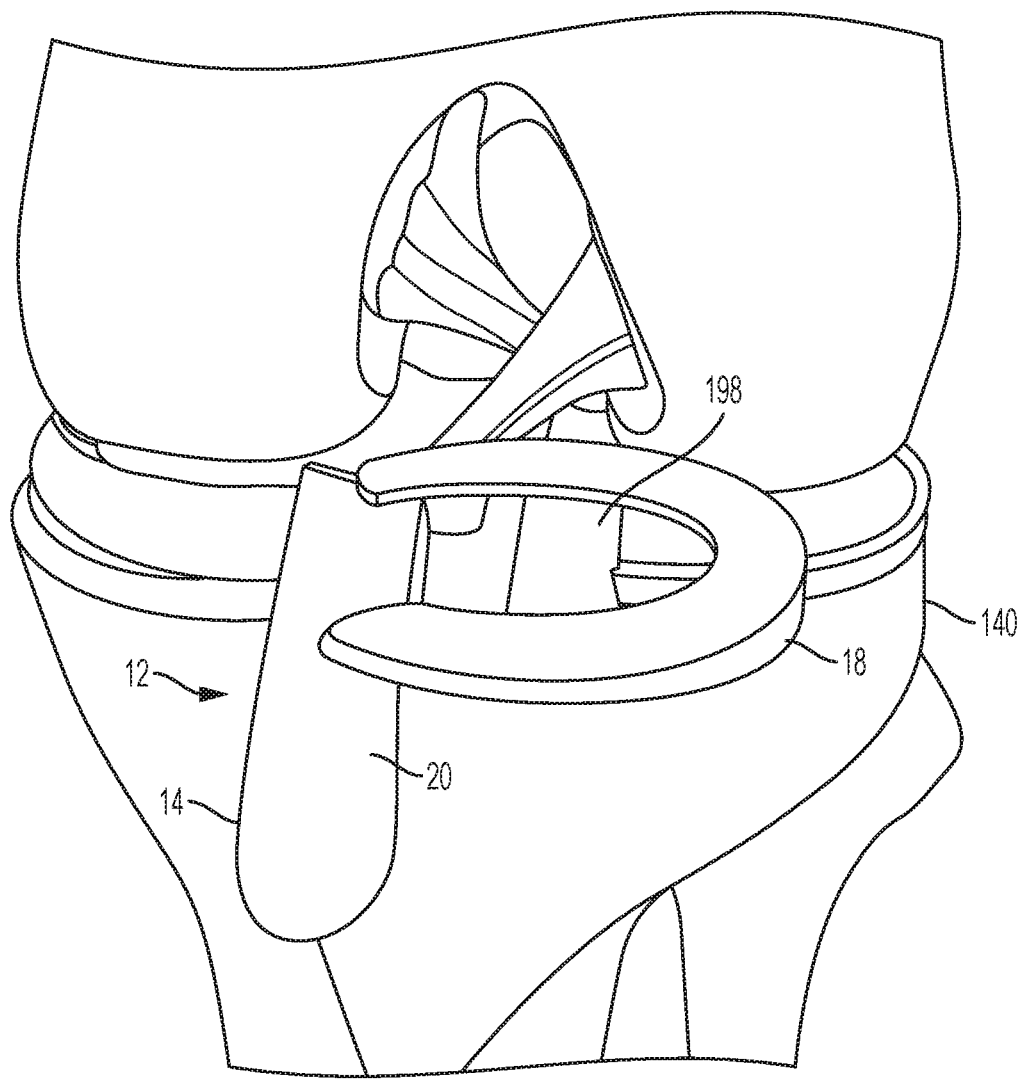
FIG. 32 is a perspective view of a meniscus graft prepared according to the present invention for implantation into a tibia prepared according to the present invention.
Figure 33:
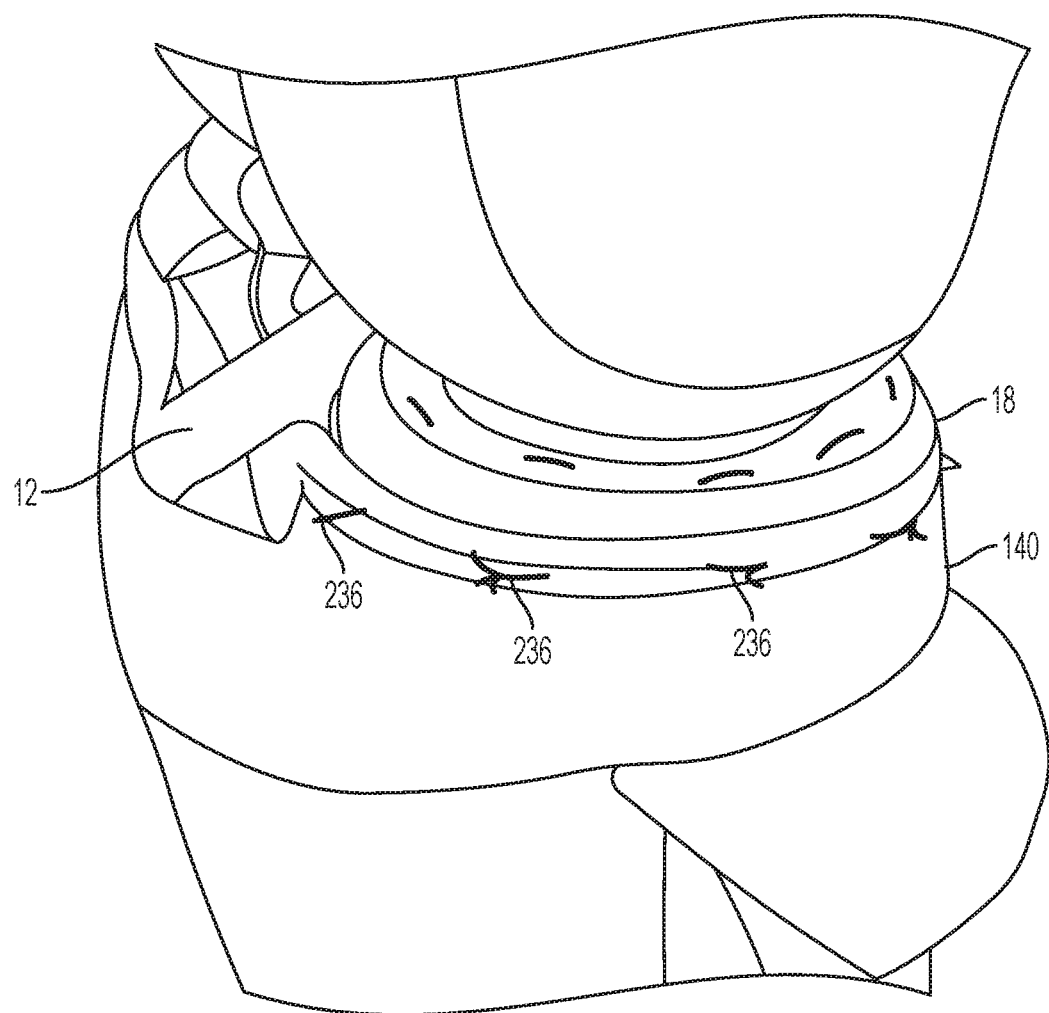
FIG. 33 is a perspective view of a meniscus graft prepared according to the present invention implanted into and sutured to a tibia according to the present invention.

Referring to FIG. 32, graft 12 may be positioned in tibia 140 by placing remaining bone portion 14 of graft 12 in the shaped hole 198 in tibia 140 so that meniscus 18 is appropriately positioned over the top of tibia 140 where the damaged meniscus was located prior to removal. Due to precise alignment and cutting of graft 12 on workstation 10, graft 12 will match the profile of hole 198 exactly and meniscal horns 22 and 24 will in the appropriate position so that meniscus 18 is in the proper location on the top of tibia 140 Once graft 12 and meniscus 18 are properly positioned, the graft meniscus 18 attached to the remnant of the patient's original meniscus by inserting a series of sutures 236 around the upper edge of tibia 140 as seen in FIG. 33.

The various tools for preparing tibia 140 as discussed above may be made from any suitable material, such as stainless steel (e.g., 17-4PH stainless steel or NITRONIC 60). Any numbers or lettering can be made using a suitable marking method, such as laser etching. Components may also be passivated after laser etching according to ASTM A967 or ASM-QQ-P-35.

What is claimed is:

1. A method for preparing a meniscus bone graft, comprising the steps of:
   clamping a donor bone part having a meniscus extending from the donor bone part by a pair of meniscal horns to against a top surface of a plate that is attached to a base of a workstation and extends along a horizontal plane using a first clamp on the workstation, wherein the first clamp comprises a post extending upwardly from a top surface of the base of the workstation and an arm coupled to the post and extending over the plate to clamp the donor bone part against the top surface of the plate;
   slidably positioning a first cutting gate over a pair of posts, said pair of posts extending upwardly from the base of the workstation on opposite sides of the plate parallel to each other to define a traversing axis extending therebetween, wherein the pair of posts extend along a plane perpendicular to the horizontal plane;
   cutting the donor bone part along a first cutting path defined through the first cutting gate that extends along a first plane that intersects with the horizontal plane of the plate at an oblique angle and that is proximally offset from the traversing axis extending between the pair of posts and the pair of meniscal horns;
   slidably positioning a second cutting gate over the pair of posts and adjusting the alignment of the second cutting gate to be parallel with an axis the extends between the pair of meniscal horns;
   cutting the donor bone part along a second cutting path defined through the second cutting gate that extends along a second plane that is parallel to the horizontal plane and in alignment with the axis of the pair of meniscal horns;
   slidably positioning a third cutting gate over the pair of posts;
   cutting the donor bone part along a third cutting path defined through the third cutting gate that extends along a third plane that intersects with the horizontal plane of the plate at an oblique angle and that is distally offset from the axis of the pair of posts and the pair of meniscal horns to form a graft having two lateral sides defined by the first and third cutting paths, a bottom defined by the second cutting path, and a top having the meniscus attached to the bone implant by meniscal horns;

placing the graft in a first groove defined in the base and attaching a second clamp to the graft;

using the second clamp to move the graft along a first shaver attached to the workstation, the first shaver having a first set of blades to shape the graft into a first shape; and using the clamp to move the graft along a second shaver attached to the workstation, the first shaver having a second set of blades to shape the graft into a second shape that is different than the first shape.

2. The method of claim 1, wherein the third cutting gate comprises the first cutting gate reversibly coupled to the posts.

3. The method of claim 2, further comprising the step of attaching a drill guide having a throughbore and an adjustable hook beam that extends from a proximal end through the drill guide proximately to the throughbore to a distal end over a tibia into which the graft is to be implanted.

4. The method of claim 3, further comprising the step of using a pilot guide inserted into the throughbore of the drill guide and a pilot drill bit having a pilot drill stop to drill a pilot hole into the tibia until the pilot drill stop contacts the proximate end of the hook beam.

5. The method of claim 4, further comprising the step of using a guide pin extended through the throughbore of the drill guide and the pilot hole and a cannulated drill bit having drill stop that can be extended through the pilot guide and over the guide pin to form an implant hole in the tibia.

6. The method of claim 5, further comprising the step of using a guide rod positioned in the implant hole and a chisel having a handle that can slidingly advance along the guide rod into the tibia to shape the implant hole until the guide rod extends into the handle of the chisel a predetermined distance.

7. The method of claim 6, further comprising the step of inserting the graft into the implant hole and suturing the meniscus to the tibia.

* * * * *